(12) United States Patent
Pederson et al.

(10) Patent No.: US 8,653,632 B2
(45) Date of Patent: Feb. 18, 2014

(54) SYSTEM AND METHOD FOR CONDITIONING IMPLANTABLE MEDICAL DEVICES

(75) Inventors: Brian Pederson, Plymouth, MN (US); Larry Peterson, Maple Grove, MN (US); Brian Hanson, Rogers, MN (US)

(73) Assignee: Medtronic ATS Medical Inc., Minneapolis, MN (US)

(*) Notice: Subject to any disclaimer, the term of this patent is extended or adjusted under 35 U.S.C. 154(b) by 750 days.

(21) Appl. No.: 12/852,836

(22) Filed: Aug. 9, 2010

(65) Prior Publication Data

US 2011/0200738 A1 Aug. 18, 2011

Related U.S. Application Data

(63) Continuation-in-part of application No. 12/238,958, filed on Sep. 26, 2008, which is a continuation-in-part of application No. 12/057,729, filed on Mar. 28, 2008.

(60) Provisional application No. 60/908,576, filed on Mar. 28, 2007.

(51) Int. Cl.
*H01L 23/58* (2006.01)
*C25D 17/06* (2006.01)

(52) U.S. Cl.
CPC .................................... *C25D 17/06* (2013.01)
USPC ........................................ 257/629; 148/422

(58) Field of Classification Search
USPC .......................................... 148/422; 257/629
See application file for complete search history.

(56) References Cited

U.S. PATENT DOCUMENTS

| | | |
|---|---|---|
| 3,609,768 A | 10/1971 | Ayres et al. |
| 3,757,794 A | 9/1973 | Cannon et al. |
| 3,914,802 A | 10/1975 | Reick |
| 4,038,702 A | 8/1977 | Sawyer |
| 4,945,912 A | 8/1990 | Langberg |
| 4,979,955 A | 12/1990 | Smith |
| 5,078,763 A | 1/1992 | Blount-Gillette |
| 5,348,553 A | 9/1994 | Whitney |
| 5,464,438 A | 11/1995 | Menaker |
| 5,578,073 A | 11/1996 | Haimovich et al. |
| 5,603,731 A | 2/1997 | Whitney |
| 5,648,330 A | 7/1997 | Pierschbacher et al. |
| 5,741,852 A | 4/1998 | Marchant et al. |

(Continued)

FOREIGN PATENT DOCUMENTS

| | | | |
|---|---|---|---|
| DE | 19814885 A1 * | 10/1999 | .............. C25D 17/06 |
| EP | 0 643 601 B1 | 8/2001 | |

(Continued)

OTHER PUBLICATIONS

R1, Electropolishing, 2004, http://en.wikipedia.org/wiki/electropolishing.*

(Continued)

*Primary Examiner* — Dah-Wei D Yuan
*Assistant Examiner* — Andrew Bowman

(57) ABSTRACT

A method for passivating a biomaterial surface includes exposing the biomaterial surface to therapeutic electrical energy in the presence of blood or plasma. The biomaterial surface may be removably secured within a chamber of a treatment system, which communicates the therapeutic electrical energy to the biomaterial surface while interfacing the biomaterial surface with blood or plasma.

17 Claims, 13 Drawing Sheets

(56) References Cited

U.S. PATENT DOCUMENTS

| | | | |
|---|---|---|---|
| 5,895,419 | A | 4/1999 | Tweden et al. |
| 5,924,975 | A | 7/1999 | Goldowsky |
| 5,986,168 | A | 11/1999 | Noishiki |
| 5,993,890 | A | 11/1999 | Marchant et al. |
| 6,013,625 | A | 1/2000 | Pierschbacher et al. |
| 6,047,700 | A | 4/2000 | Eggers et al. |
| 6,110,204 | A | 8/2000 | Lazarov et al. |
| 6,206,914 | B1 | 3/2001 | Soykan et al. |
| 6,632,215 | B1 | 10/2003 | Lemelson |
| 6,658,288 | B1 | 12/2003 | Hayashi |
| 7,071,235 | B2 | 7/2006 | Guire et al. |
| 7,132,408 | B2 | 11/2006 | Boyer et al. |
| 7,166,612 | B2 | 1/2007 | Flaumenhaft |
| 7,311,727 | B2 | 12/2007 | Mazumder et al. |
| 2001/0000802 | A1 | 5/2001 | Soykan et al. |
| 2002/0120297 | A1 | 8/2002 | Shadduck |
| 2003/0229376 | A1 | 12/2003 | Sandhu |
| 2004/0210282 | A1 | 10/2004 | Flock et al. |
| 2004/0215310 | A1 | 10/2004 | Amirana |
| 2004/0229333 | A1 | 11/2004 | Bowlin |
| 2004/0243225 | A1 | 12/2004 | Ragheb et al. |
| 2005/0021134 | A1 | 1/2005 | Opie |
| 2005/0098241 | A1* | 5/2005 | Wachter et al. ............... 148/422 |
| 2005/0143802 | A1 | 6/2005 | Soykan et al. |
| 2007/0010702 | A1 | 1/2007 | Wang et al. |

FOREIGN PATENT DOCUMENTS

| | | |
|---|---|---|
| SE | 1 566 472 | 4/1980 |
| WO | 88/01155 A1 | 2/1988 |
| WO | 93/25273 A1 | 12/1993 |
| WO | 94/11411 A1 | 5/1994 |
| WO | 94/25081 A1 | 11/1994 |
| WO | 95/19796 A1 | 7/1995 |
| WO | 99/36193 A1 | 7/1999 |
| WO | 99/44519 A1 | 9/1999 |
| WO | 03/037400 A2 | 5/2003 |
| WO | 2005/004754 A2 | 1/2005 |

OTHER PUBLICATIONS

E1, Common Wire Gauges, 2000, http://hyperphysics.phy-astr.gsu.edu/hbase/tables/wirega.html.*

Grunkemeier et al. "Platelet Adhesion and Procoagulant Activity Induced by Contct with Radiofrequency Glow Discharge Polymers: Roles of Adsorbed Fibriogen and vWF", J. Biomed Mater. Res., 51(4):669-79 (Sep. 15, 2000), Abstract.

Grunkemier et al., "The Effect of Adsorbed Fibrinogen, Fibronectin, von Willebrand Factor and Vitronectin on the Procoagulan State of Adherent Platelets", Biomaterials, 21(22):2243-52 (Nov. 2000), Abstract.

Kloczewiak et al., "Studies on Chemically Modified Fibrinogen", Thromb Haemost, 35(2):324-33 (Apr. 30, 1976).

Pfister et al., "Late Clinical Events after Clopidogrel Discontinuation May Limit the Benefit of Drug-Eluting Stents: An Oservational Study of Drug-Eluting Versus Bare-Metal Stents", J. Am. Coll. Cardiol., 48(12):2584-91 (2006), Abstract.

Qui et al., "Convienient and Effecitve Method for Removing Fibrinogen from Serum Specimens before Protein Electrophresis", Clinical Chemistry, 49(6):868-72 (2003).

Tsai et al., "Variations in the Ability of Adsorbed Fibrinogen to Mediate Platelt Adhesion to Polystryene-Based Materials: A Multivariate Statistaical Analysis of Antibody Binding to the Platelet Binding Sites of Fibrinogen", J. Biomed Mater Res A, 67(4):1255-68 (Dec. 15, 2003), Abstract.

* cited by examiner

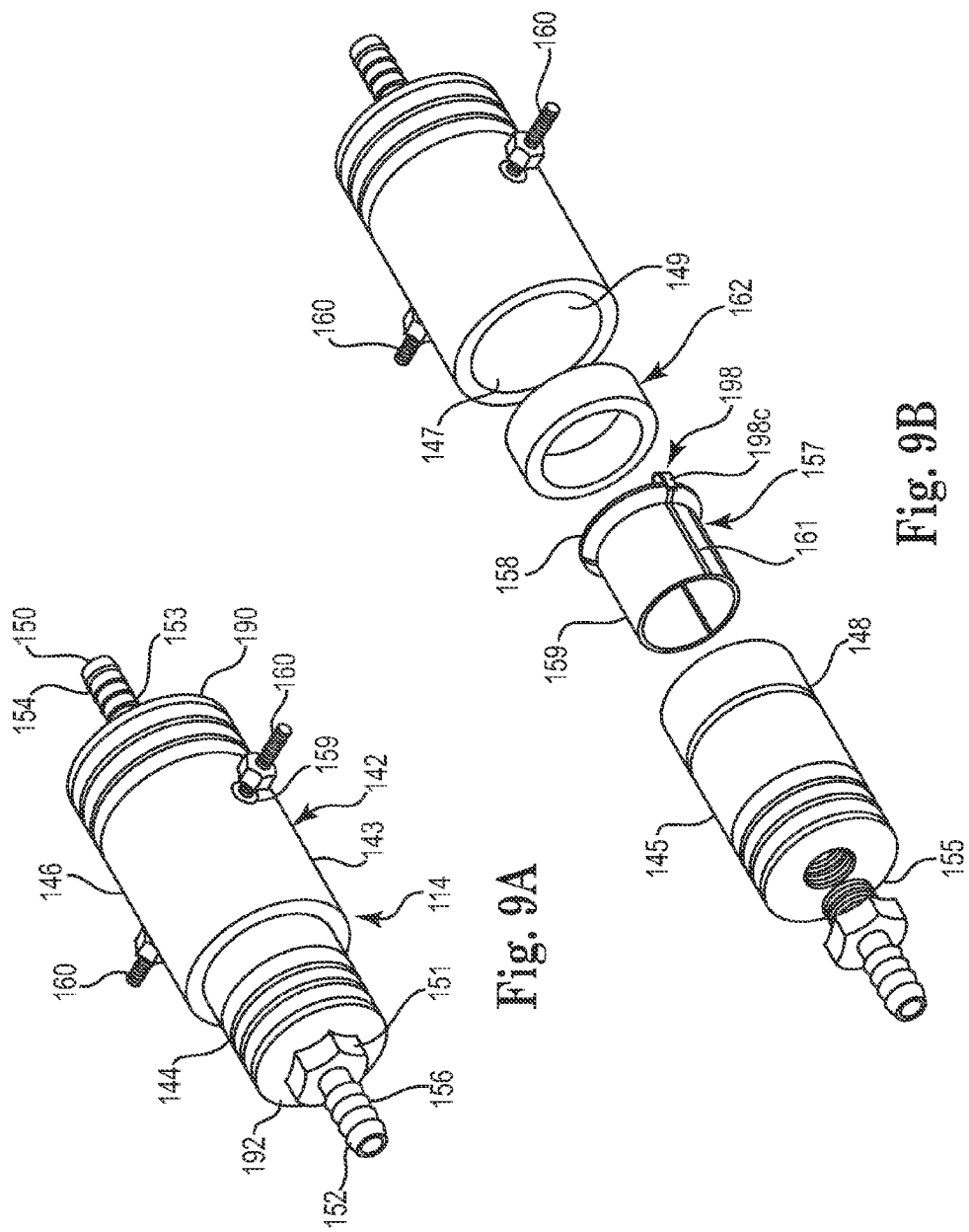

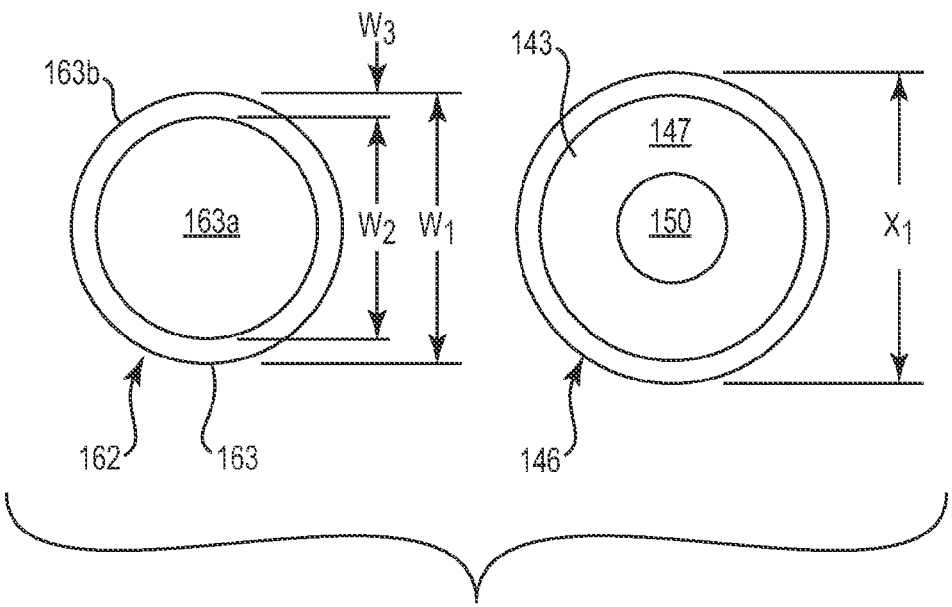
Fig. 9C
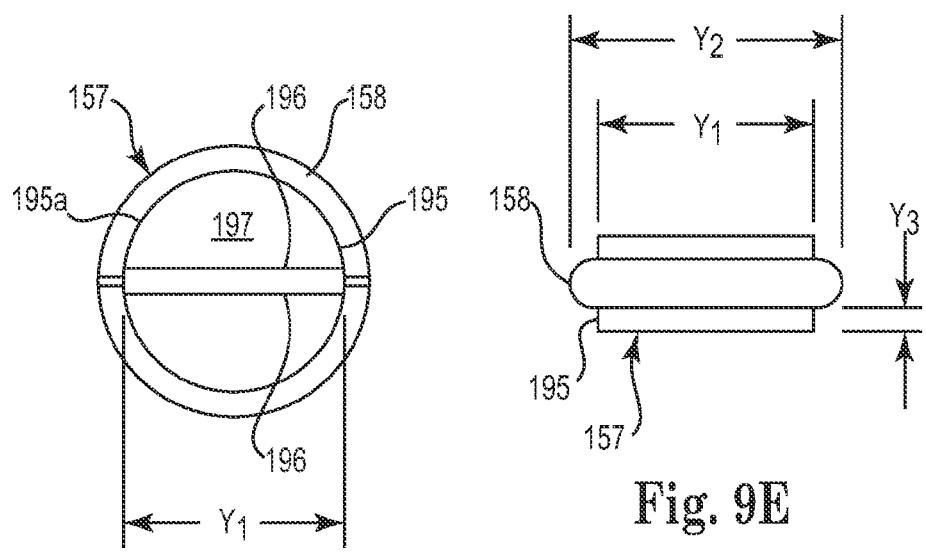
Fig. 9D
Fig. 9E

SYSTEM AND METHOD FOR CONDITIONING IMPLANTABLE MEDICAL DEVICES

CROSS-REFERENCE TO RELATED APPLICATIONS

This application is a continuation-in-part of U.S. patent application Ser. No. 12/238,958, filed on Sep. 26, 2008 and entitled METHOD FOR INHIBITING PLATELET INTERACTION WITH BIOMATERIAL SURFACES, which itself is a continuation-in-part of U.S. patent application Ser. No. 12/057,729, filed on Mar. 28, 2008 and entitled METHOD FOR INHIBITING PLATELET INTERACTION WITH BIOMATERIAL SURFACES, which itself claims priority from U.S. provisional patent application Ser. No. 60/908,576, filed on Mar. 28, 2007 and entitled METHOD FOR INHIBITING PLATELET INTERACTION WITH IMPLANTED MEDICAL DEVICES, the contents of which are incorporated herein in their entirety.

FIELD OF THE INVENTION

The present invention relates to providing biomaterial surfaces with thromboresistivity generally, and more particularly to systems and methods for passivating a biomaterial surface so as to inhibit blood platelet interaction therewith.

BACKGROUND OF THE INVENTION

Since the year 2000 alone, more than 1,000,000 vascular prosthetic devices have been implanted worldwide. From stents to artificial heart valves and ventricular assist devices, a wide range of devices are being used to treat patients often expected to live for many years after the procedures. Since biomaterials promote surface-induced thrombotic phenomena to some extent, an ever-increasing pool of patients reliant upon indefinite anticoagulant therapy has been created. This is unfortunate, as the use of drugs like heparin, warfarin and clopidogrel carries a serious risk of side effects like bleeding, bruising and serious internal hemorrhage.

The study of thrombogenetic sequence originates at platelet response to endothelium damage. Although platelets can be activated in suspension, they are by nature adhesive elements which perform their hemostatic function under flow conditions. Whereas platelets will not interact with the endothelial layer that covers the vascular tree, they will rapidly respond to a mechanically damaged vessel. Within several minutes after injury, the exposed surface will be covered by a continuous layer of platelets.

The sequence of events developing after the endothelium becomes damaged is well established. Studies with blood circulating through vascular segments mounted in specially designed chambers have clearly established that initial platelet attachment is mediated through the interaction of insoluble von Willebrand factor (VWF) bound to subendothelium with the platelet glycoprotein Ib-IX complex (GPIb-IX). Additional interactions of platelet GPIIb-IIIa (known also as integrin $\alpha_{2b}\beta_3$) with the amino acid sequence Arg-Gly-Asp-Ser (RGDS) present on several adhesive proteins (fibrinogen, VWF and fibronectin) will play a major role on platelet spreading and aggregate formation.

All major receptors on the platelet membrane are connected via GTP regulatory proteins to cytoplasmic second-messenger-generating enzymes. Coupling of receptors with their specific agonist will generate a second messenger that raises the free calcium level in platelet cytoplasm. Increased levels of Ca++ will result in the amplification of activation mechanisms with cytoskeletal assembly, internal contraction, fusion and release of the alpha granules and expression of activation dependent antigens (CD-62P) that would facilitate crosstalk interactions with leukocytes. During this process of activation anionic phospholipids will become externalized at the membranes of activated platelets. These phospholipids will further facilitate mechanism of blood coagulation.

Blood contacting biomaterial surfaces in particular, have been shown to adsorb a layer of proteins from blood and to attract platelets. Build-up of blood components on the surface of implanted devices may reduce their effectiveness, and in many cases will lead to serious adverse complications or operational failure. Thrombogenesis presents a major problem associated with the clinical use of all kinds of prosthetics, and the prevention of unwanted clotting without the side effects incurred through the use of blood thinning drugs would be a major advancement in the field of biomaterials.

One method for securing biomaterials against unwanted thrombosis is to modify the biomaterial surface itself. For example, anti-thrombogenic materials have been covalently bonded onto the blood-contacting biomaterial surfaces. Additionally, the biomaterial has been treated to give its surface a fixed charge which can affect the biocompatibility of the material. In other cases, the surface has been polished to an extremely high degree. None of these techniques, however, have been completely effective in deterring platelet adhesion to the biomaterial surface.

Platelets will avidly interact with any foreign surface including any kind of artificial material. Mechanisms responsible for the interaction of platelets with artificial surfaces are mediated by the same glycoproteins described above, though functions of these glycoproteins are not identical to those described in the previous section. It is fully accepted that the presence of proteins adsorbed on the artificial surface play a crucial role in mediating the initial interactions of platelets with the surface, and the composition of the synthetic surface is a key determinant on the rate and nature of the protein adsorbed. Vroman and Cols demonstrated the effect named as "Vroman effect", describing that a first protein was deposited on the surface after the initial contact of blood with a polymer surfaces, that initial protein was sequentially replaced by another protein. The nature of the adsorbed proteins has a critical influence on further platelet deposition. Albumin is known to inhibit platelet deposition on artificial surfaces in vitro. Contrarily to albumin, fibrinogen, fibronectin and von Willebrand factor enhance platelet interactions with the artificial surface. Two regions of the fibrinogen alpha chain that contain an RGD motif, as well as the carboxyl-terminus of the fibrinogen gamma chain, represent potential binding sites for GPIIb-IIIa in the fibrinogen molecule.

In essence, while the initial attachment of platelets with vascular subendothelium is initiated through interactions of GPIb-IX with vWF bound to collagen, the interaction of platelets with artificial surfaces may be considered to be mainly driven by GPIIb-IIIa and fibrinogen adsorbed onto the surfaces.

It has been theorized that promoting adhesion of albumin to the detriment of fibrinogen at the blood-contacting surface could be effective in altering the thrombogenicity of various materials. In fact, Grunkemeier et al., *Biomaterials*, November, 2000 pp. 2243-2252, and Tsai et al., *Journal of Biomedical Materials Research* Dec. 15, 2003, pp. 1255-68, found that the amount of adsorbed fibrinogen was the chief determinant of the degree of platelet adhesion, although platelets were most attracted to a surface when a combination of proteins was residing on the surface, including Von Willebrand factor. No preadsorption of particular blood proteins has yet been shown to prevent clotting entirely. It is very difficult to prevent fibrinogen from adhering to the biomaterial surface, and only a small amount of adhered fibrinogen is necessary to start a chain reaction leading to thrombosis.

Some materials coated with anticoagulant agents such as heparin have had limited success in preventing thrombosis. However, heparin coatings will eventually dissolve over time. Drawbacks to agent-eluting surfaces have also been realized. A study by Pfisterer et al., *Journal of American College of Cardiologists*, Dec. 19, 2006 pp. 2592-5 regarding the Basel Stent Kosten Effektivitats Trial, Late Thrombotic Events, suggested that between 7 and 18 months after implantation, the rates of nonfatal myocardial infarction, death from cardiac causes, and angiographically documented stent thrombosis were higher with drug-eluting stents than with bare metal stents.

Overall, there have been no recognized clinical advancements that could warrant replacing traditional anticoagulation therapy. At this time, only consistent maintenance of a regimen of blood thinning agents is clinically proven to prevent the dangerous thrombotic events associated with implants.

It is an object of the present invention to provide a system for conditioning a biomaterial surface to provide an anti-thrombogenic characteristic thereto.

It is another object of the present invention to provide a method for establishing an anti-thrombogenic characteristic to biomaterial surfaces, including surfaces of an implantable medical device.

It is a further object of the present invention to provide a packaging and delivery system for an implantable medical device.

SUMMARY OF THE INVENTION

By means of the present invention, biomaterial surfaces may be provided with a thromboresistant characteristic, such that blood-contacting surfaces of a biomaterial inhibits blood platelet interaction and adhesion therewith. Such passivation of the biomaterial surface is effectuated through a passivating procedure, which may involve application of therapeutic electrical energy and/or deposition of certain proteinaceous materials thereat. Biomaterial surface passivation may be accomplished in vivo, ex-vivo, or in vitro, and may be done prior to, or subsequent to implantation of a biomaterial in a patient.

In one embodiment, a method for passivating a biomaterial surface involves exposing the biomaterial surface to therapeutic electrical energy in the presence of blood or plasma.

BRIEF DESCRIPTION OF THE DRAWINGS

FIG. 9A is an assembly view of a treatment system of the present invention;

FIG. 9B is an exploded view of the assembly of FIG. 9A;

FIG. 9C is an isolation view of portions of the treatment system illustrated in FIG. 9A;

FIG. 9D is an isolation bottom view of an example medical article useful in the treatment system of the present invention;

FIG. 9E is an isolation side elevational view of the medical article illustrated in FIG. 9D;

DETAILED DESCRIPTION OF THE PREFERRED EMBODIMENTS

The objects and advantages enumerated above together with other objects, features, and advances represented by the present invention will now be presented in terms of detailed embodiments. Other embodiments and aspects of the invention are recognized as being within the grasp of those having ordinary skill in the art.

The present invention is drawn to techniques and materials which have been found to be useful in inhibiting platelet interaction with biomaterial surfaces. Such interaction may include, for example, adhesion, aggregation, thrombosis, clotting, and/or coagulation of blood platelets at a biomaterial surface exposed to such platelets. For the purposes of this application, the terms "passivate", "passivated", or "passivating" shall refer to a surface that exhibits anti-thrombogenic properties so as to inhibit thrombosis thereat. In some instances, such term may further connote improving the biocompatibility of the surface, such as through thromboresistant properties. For the purposes of this application, "thromboresistant" and "anti-thrombogenic" may be used interchangeably.

A variety of biomaterials may be passivated through the present invention. Most commonly, however, biomaterials include those materials thought to be useful in the fabrication of medical articles, such as implantable medical articles. However, the techniques and materials of the present invention may indeed facilitate the use of "biomaterials" which, in the absence of the techniques and materials of the present invention, would not typically be considered in medical applications, such as in implantable medical articles. Accordingly, as used herein, "biomaterials" is intended to include any native, natural, and/or artificial material used in a biological application, such as in the contacting of blood, plasma, or other biological fluids. Example biomaterials may include metal such as stainless steel, nitinol, and titanium, plastics such as polyolefins, polyesters, polystyrenes, polyurethanes, polyamides, polytetrafluoroethylenes, polysiloxanes, polyimides, phenolics, amino-epoxy resins, polyacrylonitriles, polymethacrylates, silicones, and silicone rubbers, as well as other materials such as pyrolytic carbon and ceramics. In some embodiments of the invention, electrically conductive materials, such as those having an electrical resistivity of less than about 5 ohms may be utilized, though such resistivity threshold may be overcome by using higher voltage potentials. The biomaterials may be used in medical articles including vascular stents, grafts, heart valves, heart diaphragms, catheters, implantable pacemakers, defibrillators, and related leads, sutures, needles, tubing, dialysis membranes, filters, and the like.

Figure 8:
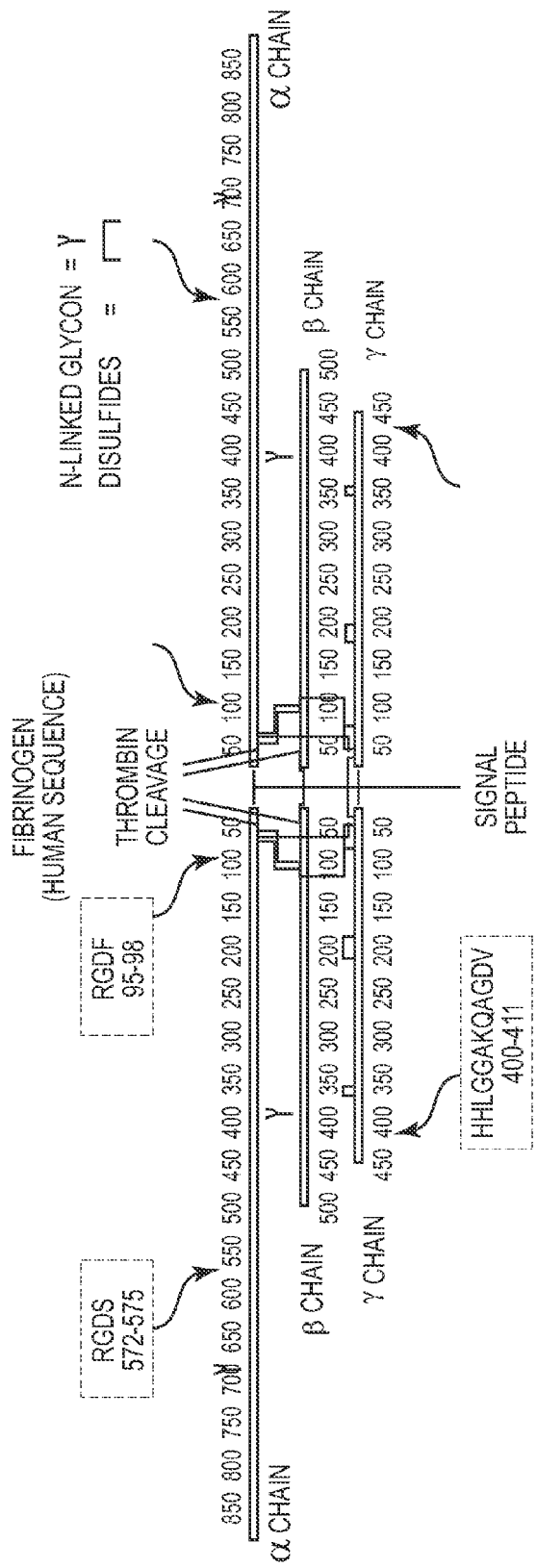
FIG. 8 is a schematic representation of the molecular structure of fibrinogen.

The Applicant has focused studies on the thromboresistant properties exhibited by proteinaceous materials contained in or derived from blood. Example such proteinaceous materials that have been addressed in this effort include albumin and fibrinogen. One thromboresistant factor that has been developed in the present studies is a conformationally altered fibrinogen. In its standard form, fibrinogen includes three distinct "conformations", each having slightly different molecular weights. These may be referred to as alpha, beta, or gamma fibrinogen. Such distinct conformations can be viewed through gel electrophoresis, wherein three distinct bands are prevalent at about 50 kD. As shown in FIG. 8, fibrinogen contains three putative platelet interaction sites, namely the sequence Arg-Gly-Asp-Phe (RGDF) at $A\alpha^{95-98}$, the sequence Arg-Gly-Asp-Ser (RGDS) at $A\alpha^{572-575}$, and the dodecapeptide sequence His-His-Leu-Gly-Gly-Ala-Lys-Gln-Ala-Gly-Asp-Val (HHLGGAKQAGDV) at $\gamma^{400-411}$. Both the RGDS, and the dodecapeptide sequence play a key role in platelet aggregation.

Subsequent to exposure to the electrical energy as described herein, the relative concentrations of the fibrinogen conformations at the biomaterial surface are modified. In one embodiment, at least one of the three fibrinogen conformations exposed to the therapeutic electrical energy is found at significantly higher concentrations at a surface exposed to the electrical energy than the concentration of such fibrinogen conformation at a surface not exposed to the therapeutic electrical energy. In addition, at least one fibrinogen conformation concentration is significantly decreased upon electrical stimulation.

The inmovilization and the conformational change in the fibrinogen molecule exposes specific sites for the GPIIb-IIIa receptor in the platelet membranes [31]. It has been postulated that the presence of two γ-chain carboxyl-terminal domains in the dimeric fibrinogen molecule may influence the adhesion of nonstimulated platelets when the ligand is immobilized onto a surface [32]. If these interpretations are correct, the γ-chain of the fibrinogen would play a more important role mediating the interaction of platelets with fibrinogen bound to surfaces.

Figure 6:
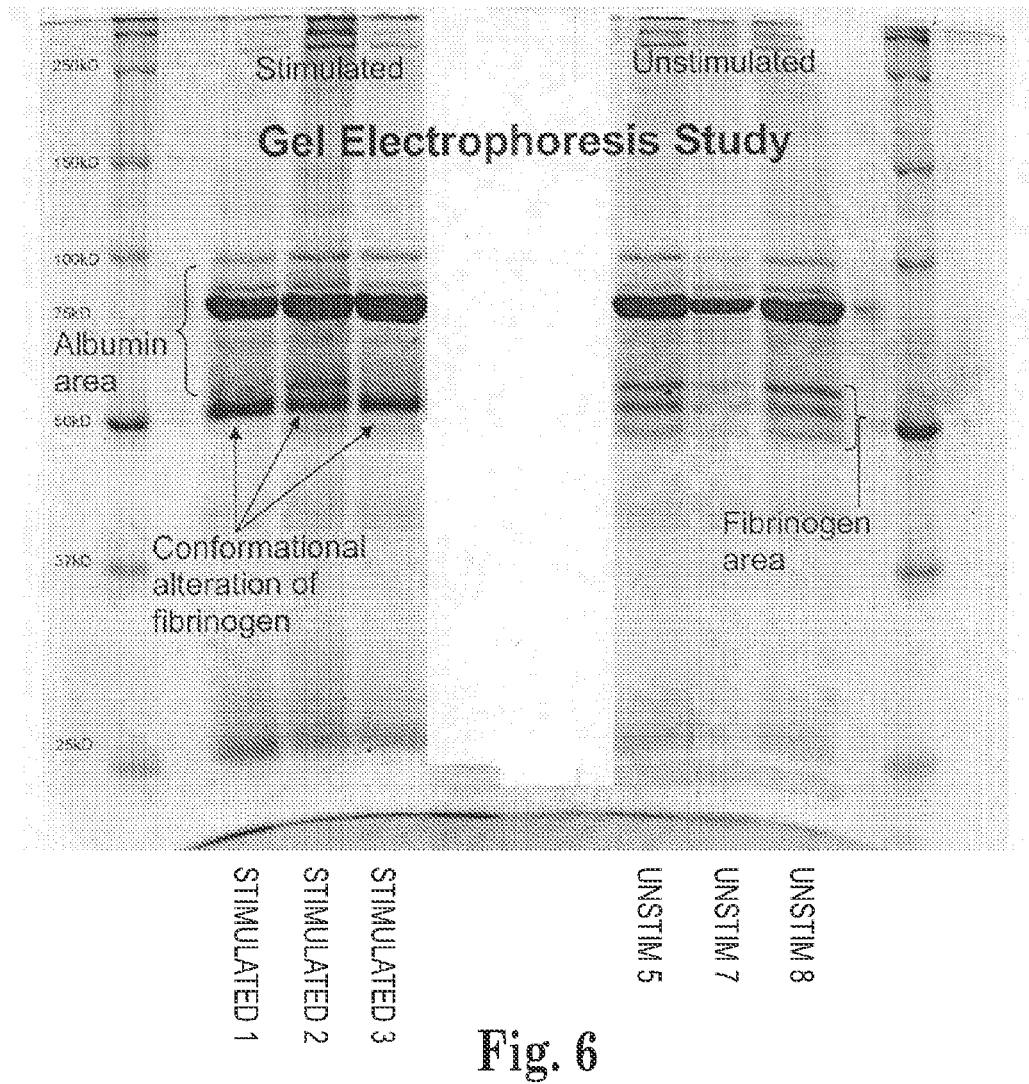
FIG. 6 is a series of gel electrophoresis images comparing surfaces of test articles in a stimulated environment with test articles in an unstimulated environment.

Interestingly, the evidence provided by FIG. 6 indicates qualitative changes in the fibrinogen molecule deposited on the stimulated surfaces. The 3 bands around 50 kD corresponding to the alpha, beta and gamma chains of fibrinogen are well preserved in surfaces non exposed to the electrical field technology. Application of specific electrical energy to the same surface resulted in an increased presence of the β chain of fibrinogen with an evident reduction in the presence of α and γ chains of fibrinogen. These observations may reflect a conformational alteration of fibrinogen. It is hypothesized that the binding factor of fibrinogen to blood platelets is modified or eliminated through the fibrinogen conformational adjustment described above. As such, the conformationally altered fibrinogen has little or no adhering interaction with blood platelets, thereby effectuating a thromboresistant characteristic.

Another thromboresistant factor of the present invention is the preferential promotion of albumin adhesion to a biomaterial surface. Biomaterials having a relatively high surface concentration of albumin have been shown to inhibit fibrin cascade and platelet attachment, potentially through disruption of electric charge-related platelet interactions. Typically, however, fibrinogen is often the dominant protein adsorbed from protein mixtures such as blood, blood serum, or plasma. Because fibrinogen, in its standard form, is known to promote platelet adhesion at a surface, preferential albumin adsorption acts to inhibit platelet adhesion both through the thromboresistant properties of albumin and through the reduction of fibrinogen presence at the surface.

One technique for effectuating one or more of the thromboresistant factors described above at a biomaterial surface involves the application of electrical energy to proteinaceous material found in blood and/or the application of electrical energy to a biomaterial surface while in the presence of such proteinaceous material. The application of electrical energy, such as a magnitude of electrical energy deemed therapeutic, to blood or plasma has surprisingly been found to cause thromboresistance in biomaterial surfaces contacted with the treated blood or plasma. It is theorized that the thromboresistance generated at the biomaterial surface is derived from one or both of the presence of conformationally altered fibrinogen and the disproportionately high concentration ratio of albumin to standard fibrinogen at such biomaterial surface. Moreover, it is theorized that the existence of such thromboresistant factors at the biomaterial surface is created through the application of therapeutic electrical energy to proteinaceous material contained in blood, blood serum, or plasma, wherein such proteinaceous material includes albumin and/or fibrinogen. Through experimentation, Applicant has determined that application of electrical energy, in the therapeutic magnitudes described herein, establishes an environment for the creation of a thromboresistant, passivated biomaterial surface characteristic. Applicant contemplates, however, that alternative methods may be employed to establish the thromboresistant factors described herein, and to provide a biomaterial surface with one or more of such factors.

In one embodiment, a biomaterial surface may be passivated by exposing such biomaterial surface to therapeutic electrical energy in the presence of blood or plasma. In another embodiment, a biomaterial surface may be passivated by exposing such biomaterial surface to blood or plasma which has been treated with therapeutic electrical energy. In a further embodiment, a biomaterial surface may be passivated by adsorbing at such surface blood proteins treated with therapeutic electrical energy. In another embodiment, a thromboresistant biomaterial surface may be achieved through the provision of a conformationally altered fibrinogen thereat. Other embodiments in addition to those described above are also contemplated as being within the scope of the present invention.

Investigations have been conducted into the prevention of biomaterial surface/platelet interaction with the application of electric current to various materials. Initial studies have focused on the reaction of pyrolytic carbon, stainless steel, nitinol, and titanium. Currently marketed cardiac and vascular stents are primarily made of stainless steel (also carbon coated), and nitinol. In initial experiments, pyrolytic carbon was chosen due to previous experience with this material. The type and magnitude of electrical energy (frequency and current) needed to provide thromboresistance on the surface of carbon have been investigated using an in-vitro blood perfusion system, as described below. Assessment of the reactions has been accomplished through scanning electron microscopy (SEM), electrophoresis, Indium (radioactive) platelet labeling, protein assay assessment, and Fluorochrome-labeled antibody staining.

Test System

Figure 1:
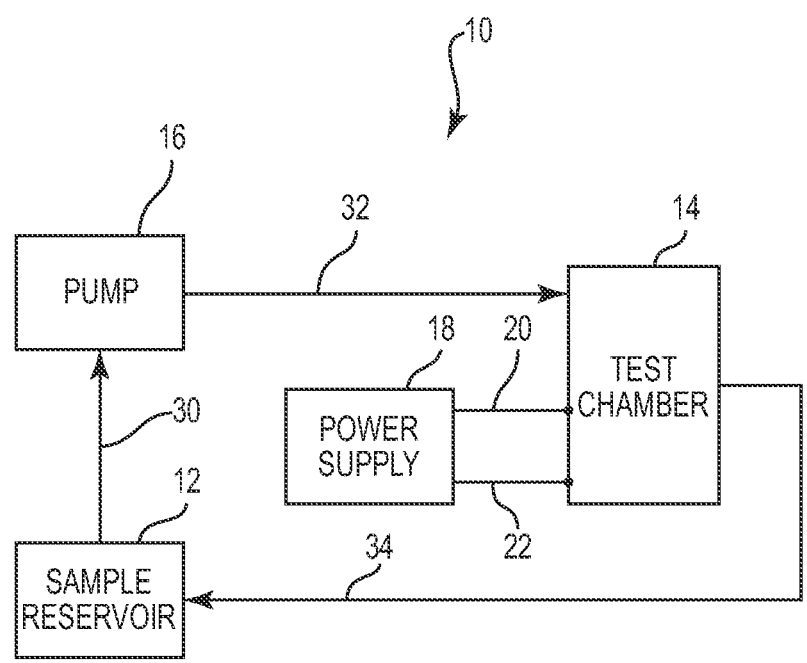
FIG. 1 is a schematic diagram of a testing apparatus used in the testing of the materials and methods of the present invention.

A blood perfusion system (BPS) was developed for the evaluation of the biomaterial surfaces and its reaction to blood, and was designed to hold any one of the biomaterials of interest. A schematic diagram of blood perfusion system 10 is illustrated in FIG. 1, and includes a sample reservoir 12, a treatment chamber 14, and a fluid pump 16 for pumping sample fluid throughout system 10. An electrical power supply 18 is electrically coupled to treatment chamber 14 through electrical leads 20, 22, and may controllably apply electrical energy to treatment chamber 14. System 10 further includes fluid conduit sections 30, 32, 34 for transporting the sample fluid throughout system 10.

Sample reservoir 12 of system 10 may be any type of reservoir for the fluids utilized in the test procedure. By way example, such fluids may include whole blood, platelet-rich plasma, or platelet-poor plasma. In some cases, a suspension such as sodium citrate or sodium heparin may be added to the fluid to inhibit spontaneous clotting. Sample reservoir 12 in the test apparatus was a 0.5 liter glass bottle.

Both a pulsatile pump and a roller pump were utilized as pump 16 of system 10. The roller pump, which was a Model 323 pump manufactured by Watson Marlow was utilized in continuous flow regimes at a flow rate of 600 ml per minute. A MOX106 pulsatile pump manufactured by Waters Instruments was calibrated to mimic a beating human heart, wherein a pump surge rate of 70-80 surges per minute was set with an output volume of 50 ml per surge. Pump 16 pumped the sample fluid throughout conduit sections 30, 32, 34, which comprise silicon rubber tubing. In particular, pump 16 pumps the sample fluid from sample reservoir 12 to treatment chamber 14, and then back to sample reservoir 12.

Figure 2:
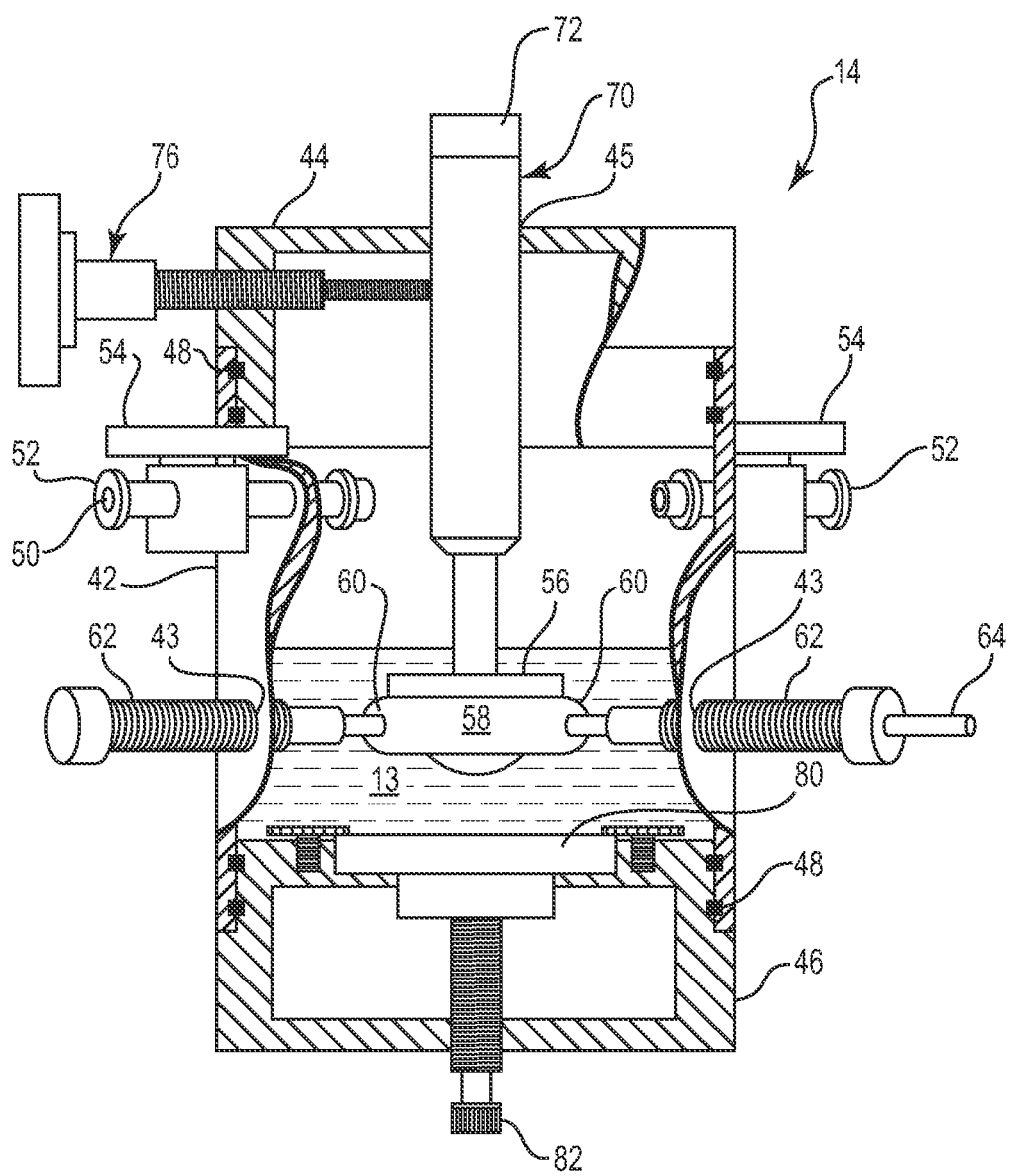
FIG. 2 is a partial cut-away view of a portion of the testing apparatus illustrated in FIG. 1.
Figure 3:
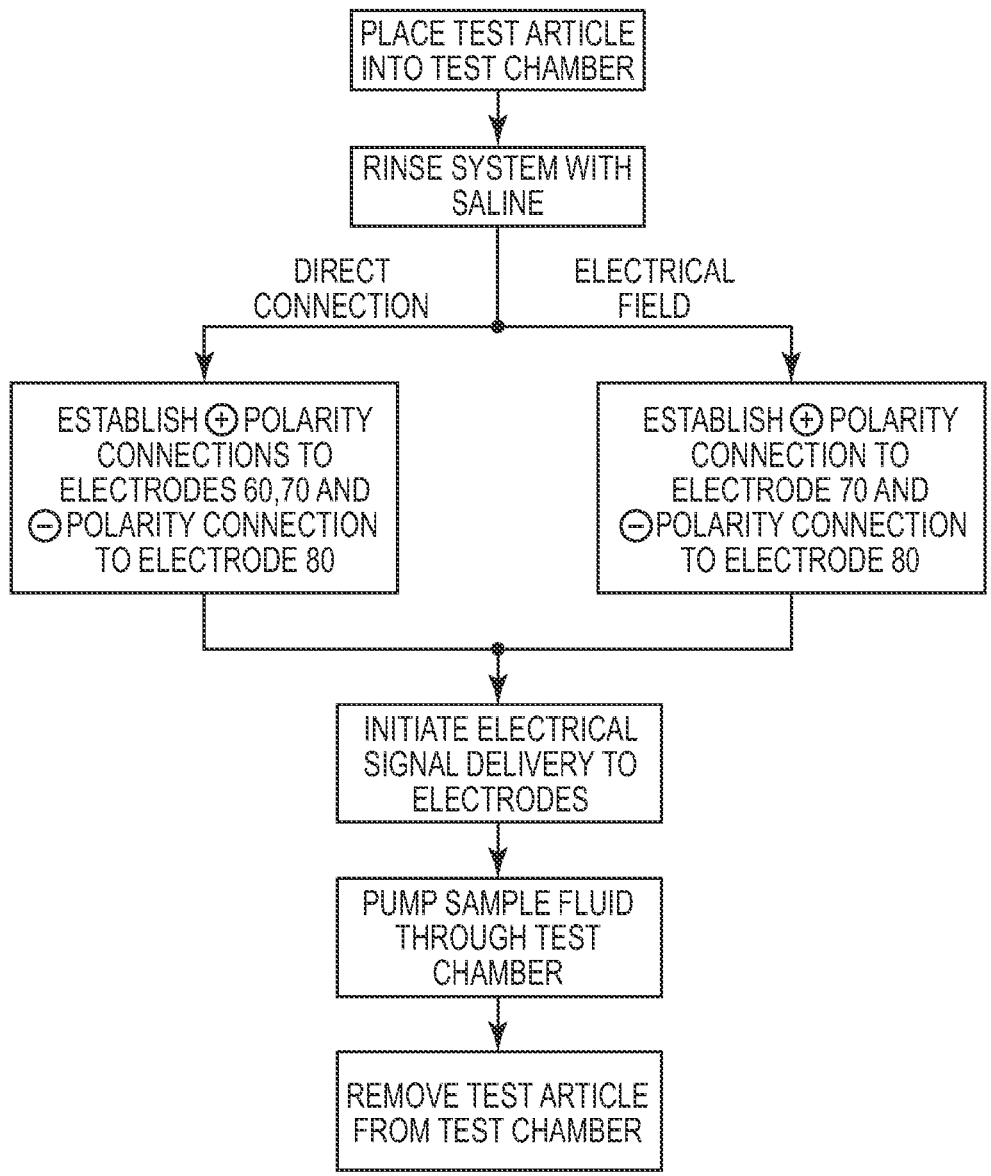
FIG. 3 is a process flow diagram of the testing procedure for testing the methods and materials of the present invention.

A first embodiment of treatment chamber 14 is illustrated in greater detail in FIG. 2, wherein treatment chamber 14 includes a polycarbonate housing 42, a top lid 44 and a bottom lid 46. The top and bottom polycarbonate lids 44, 46 are sealingly engageable with housing 42 via O-rings 48. The sample fluid is supplied to treatment chamber 14 at fluid inlet 50, and is removed from treatment chamber 14 at fluid outlet 52. Valves 54 are positioned at fluid inlet and fluid outlet 50, 52 for additional control of fluid flow through treatment chamber 14. An example biomaterial surface disposed in treatment chamber 14 is a prosthetic bi-leaflet heart valve 56 fabricated from pyrolytic carbon, and further provided with a fabric suture cuff 58 in conventional fashion. The prosthetic heart valve may be a 25 mm ATS Open Pivot™ aortic valve having a leaflet surface area of about 12.4 cm².

To suspend the valve prosthesis within treatment chamber 14, a titanium pin retainer 60 with electrically insulative plastic covers 62 may be retained at apertures 43 of housing 42, with the pin retainer 60 piercing the fabric suture cuff 58 of valve prosthesis 56. At least one pin retainer 60 is placed into contact with the pyrolytic carbon body of valve prosthesis 56 so as to make electrical contact to at least the valve body of valve prosthesis 56. In addition, such at least one pin retainer includes an exposed extension portion 64 to which electrical connection may be made. This pin retainer 60 thus forms an electrode for establishing direct electrical contact with valve prosthesis 56. A further electrode 70 is provided through an aperture 45 in top lid 44, with titanium electrode 70 extending into the chamber defined by housing 42 and into contact with the valve leaflets of valve prosthesis 56. In this manner, direct electrical contact to valve prosthesis 56 may be established by connecting an electrical lead to connection end 72 of electrode 70. A set screw 76 may be utilized in order to adjust the vertical position of electrode 70 within treatment chamber 14, and particularly into and out from electrical contact with valve prosthesis 56.

A still further electrode 80 may be provided in treatment chamber 14, wherein titanium electrode 80 is exposed to the sample fluid 13, but is spaced from valve prosthesis 56. Electrical connection to electrode 80 may be made at connection end 82 thereof. As illustrated in FIG. 2, the level of sample fluid 13 is typically above valve prosthesis 56, such that valve prosthesis 56 is operably submerged in the sample fluid 13 during the treatment procedure.

Power supply 18 may include a combination of a Tektronix™ AFG310 arbitrary waveform generator which is capable of producing multiple electrical waveforms (sin, triangular, square, and pulsatile) and a custom precision voltage to current converter capable of delivering various current levels. Electrical leads from power supply 18 are connected to respective ones of the electrodes 60, 70, 80 during the treatment procedure. In some cases, positive polarity is coupled to both electrodes 60 and 70 while negative polarity is coupled to electrode 80. In other cases, positive polarity is coupled only to electrode 70 while negative polarity is coupled to electrode 80. Electrical connection is established at the terminus of the electrical leads through conventional electrical clips.

Figure 9F:
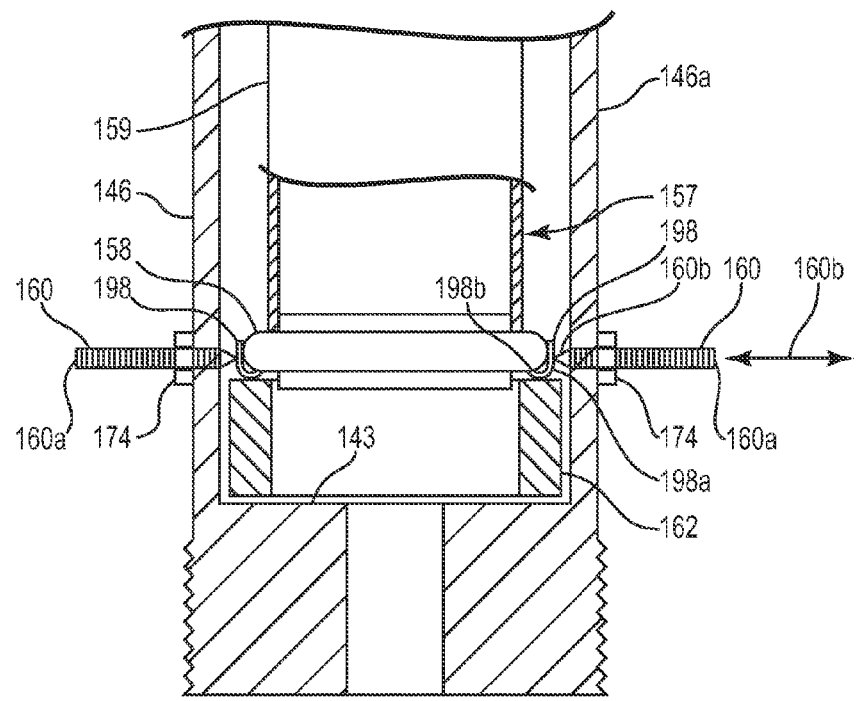
FIG. 9F is a partial cross-sectional view of the treatment system illustrated in FIG. 9A.

A second embodiment of treatment chamber 114 is illustrated in FIGS. 9A and 9B, wherein FIG. 9B is an exploded view of the assembly of treatment chamber 114. As illustrated therein, treatment chamber 114 includes a housing 142 having first and second portions 144, 146 which are sealingly engagable with one another via one or more O-rings 148. In the illustrated embodiment, first portion 144 may be engagable within second portion 146, such that an O-ring 148 disposed at an outer surface 145 of first portion 144 sealingly engages between outer surface 145 of first portion 144 and inner surface 147 of second portion 146. Such sealing engagement may preferably be fluid-tight to prevent treatment fluid from escaping from within treatment chamber 114 or air from entering treatment chamber. In one embodiment, housing 142 may be fabricated from a durable and biologically inert and electrically insulative material, such as various polymeric and insulated metal materials. In one example, housing 142 is fabricated from polycarbonate plastic, though it is contemplated that housing 142 may also or instead be fabricated from electrically insulated stainless steel, titanium, or other plastics, metals, or metal alloys. Housing 142 may be fabricated from a non-electrically conductive material, so as to focus electrical energy solely at electrically conductive components of treatment chamber 114.

In the illustrated embodiment, treatment chamber 114 is arranged such that treatment fluid is supplied at fluid inlet 150, and exits from treatment chamber 114 at fluid outlet 152. Each of fluid inlet and outlet 150, 152 form a portal to the interior 149 of housing 142. In one embodiment, treatment fluid inlet and outlet 150, 152 are defined by respective coupling elements 154, 156 engaged with respective ends 190, 192 of housing 142. Coupling elements 154, 156 may comprise dual-ended tube couplers having a first barbed end portion 153 and a second threaded end portion 155 for threadably engaging housing 142. Barbed end portion 153 may be configured to insertably engage within an inner diameter of treatment fluid conveyance tubing.

Coupling units 154, 156 may be fabricated from a biologically inert material, such as Teflon™, nylon, or other polymeric or metallic material. As illustrated, coupling units 154, 156 may further include an actuation portion 151 that may be shaped to operably engage with a tool for rotatably engaging coupling units 154, 156 with housing 142. As in conventional such devices, coupling units 154, 156 define a passageway as the portal at treatment fluid inlet and outlet 150, 152. In such a manner, the passageways of coupling units 154,156 are arranged to operably convey treatment fluids into and out from interior 149 of treatment chamber 114.

An example biomaterial surface disposed in treatment chamber 114 is a prosthetic bi-leaflet heart valve 157, and further provided with a fabric suture cuff 158 in conventional fashion. In one embodiment, the prosthetic heart valve 157 may be an ATS Open Pivot™ aortic heart valve fabricated from pyrolytic carbon.

In one embodiment, device 157 may be initially secured to a device holder 159 for use in the surgical theater. In the illustrated example, device holder 159 is arranged to support sutures 161 which initially secure device 157 to holder 159. In typical embodiments, holder 159 may be engaged to device 157 at a circumaxial surface that is not in need of treatment through the system and method of the present invention.

To suspend device 157 within treatment chamber 114, a seat member 162 may be disposed in interior 149 of second portion 146, with seat portion 162 positioning device 157 (and holder 159) within treatment chamber 114. Though the apparatus of FIGS. 9A and 9B may be particularly adapted for the treatment of a prosthetic heart valve 157, it is to be understood that appropriate modifications may be made to treatment chamber 114, and its pertinent parts, to accommodate implantable devices other than prosthetic heart valves.

As illustrated in FIG. 9C, seat member 162 includes an outer diameter "$W_1$" and an inner diameter "$W_2$" that is separated from outer diameter $W_1$ by a wall 163 having a wall thickness "$W_3$". Second portion 146 of housing 142 includes an inner diameter "$X_1$" defining a portion of interior 149. In one embodiment, seat member 162 may be operably disposed substantially concentrically within second portion 146 at interior 149. Outer diameter $W_1$ of seat member 162 may be slightly smaller than inner diameter $X_1$ of second portion 146. In this manner, seat member 162 may fit somewhat snugly concentrically within second portion 146.

As illustrated in FIG. 9A, seat member 162 may be operably positioned in juxtaposition with first interior end wall 143 of second portion 146. In this arrangement, wall 163 of seat member 162 establishes a seating surface 163b upon which device 157 may be operably positioned within treatment chamber 114.

An example prosthetic heart valve 157 is schematically illustrated in FIG. 9D, as viewed in the direction of blood flow, and in the case of treatment chamber 114, the direction of treatment fluid flow. Prosthetic heart valve 157 includes a suture cuff 158 secured about an annulus 195, which annulus 195 defines the chamber in which valve leaflets 196 operate. Annulus 195 may have an outer diameter "$Y_1$" that is substantially equal to, but slightly smaller than inner diameter $W_2$ of seat member 162. As shown in FIG. 9E, annulus 195 protrudes axially from suture cuff 158 by a dimension "$Y_3$". As a result, annulus 195 of device 157 may substantially concentrically fit within an opening 163a in seat member 162 defined by wall 163. The dimensional difference between outer diameter $Y_1$ of annulus 195 and inner diameter $W_2$ of seat member 162 may be sufficiently small so as to form a relatively snug concentric fitment as between annulus 195 and wall 163 to securely position device 157 at seat member 162. Moreover, suture cuff 158 has an outer diameter of "$Y_2$", which is larger than inner diameter $W_2$ of seat member 162. Consequently, suture cuff 158 of device 157 operably rests against seating surface 163b of wall 163 when annulus 195 is concentrically positioned in opening 163a. Such an arrangement, therefore, positions and orients device 157 at seat member 162.

The positioning of device 157 at seat member 162, as described above, also presents the blood-contacting surfaces of device 157 in the path of treatment fluid flow through treatment chamber 114. Treatment fluid flow enters treatment chamber 114 at fluid inlet 150, and passes through coupling member 154 to interior 149 of second portion 146. As described above, seat member 162 is concentrically positioned within interior 149 at first end wall 143, such that opening 163a of seat member 162 is axially aligned with fluid inlet 150. Such alignment permits treatment fluid flow through opening 163a of seat member 162, and into contact with the blood-contacting surfaces of device 157 operably positioned at seat member 162. Treatment fluid flow passes through opening 163a into chamber 197 of device 157 to come into contact with, for example, annulus 195, leaflets 196, and all other structures within the boundary defined by annulus 195. Moreover, treatment blood flow also contacts axial end surfaces 195a of annulus 195, as such surfaces are in the treatment fluid flow path channeled by opening 163a.

Device 157 is secured in place within treatment chamber 114 through the use of pin retainers 160 which extend through second portion 146 into interior 149. A schematic illustration of pins 160 operably retaining device 157 in treatment chamber 114 is provided in FIG. 9F. In particular, pins 160 may extend through a wall 146a of second portion 146 to engage with respective conductor clips 198 secured to device 157. In the illustrated embodiment, pins 160 may be threaded rods of electrically conductive material, such as titanium, stainless steel, nitinol, and the like. Threaded rods 160 may have an electrical resistance of less than about 0.5 ohms. Threaded rods 160 may be selectively threaded through wall 146a to selectively move threaded rods 160 into and out from engagement with conductor clips 198 at device 157. Nuts 174 may engage with o-rings 159 to both sealingly engage pins 160 within wall 146a to prevent fluid leakage around pins 160, and to arrest pins 160 in a desired position through wall 146a.

Pins 160, such as threaded rods 160, may be selectively actuated through, for example, a torque wrench (not shown) at respective engagement ends 160a to impart a rotational movement to pins 160, which, in turn, effectuates a movement of pins 160 along axis 160b. In one embodiment, at least two pins 160 may be placed at opposite sides of second portion 146, so as to impart substantially directly opposed compression forces to device 157 at the engagement locations between pins 160 and conductor clips 198. Such compression forces act to secure device 157 in place within treatment chamber 114.

In addition to the compression forces securing device 157 within treatment chamber 114, the electrical conductivity of pins 160 is additionally useful in conducting electrical current to device 157. In the illustrated embodiment, conductor clips 198 may be fabricated from electrically conductive material having a resistance of less than about 0.5 ohms. In one embodiment, conductor clips 198 are fabricated from titanium to efficiently conduct electrical current from pins 160 to electrically conductive portions of device 157. It is contemplated that device 157 may be fabricated primarily from an electrically conductive material, such as pyrolytic carbon. In the illustrated embodiment, the prosthetic heart valve 157, with the exception of suture cuff 158, may be fabricated from, for example, pyrolytic carbon. To effectively communicate electrical current from pins 160 to electrically conductive portions of device 157, conductor clips 198 are positioned at least partially about suture cuff 158, with a first portion 198*a* of conductor clips 198 being radially outwardly disposed from suture cuff 158 and in electrical contact with pins 160, while a second portion 198*b* of conductor clips 198 may be disposed between annulus 195 and suture cuff 158, so as to be in electrical contact with electrically conductive annulus 195. The compression forces described above further act to establish good electrical contact as between pins 160 and conductor clips 198, as well as between conductor clips 198 and device 157.

In one embodiment, pins 160 include a tapered tip 160*b* that is engagable with a recess 198*c* of conductor clips 198. Recess 198*c* "centers" pins 160 at conductor clips 198 to ensure appropriate alignment and electrical contact between pins 160 and conductor clips 198.

In addition to acting as an apparatus for passivating device 157, treatment chamber 114 may also constitute packaging for sterile storage and shipment of device 157. For example, device 157 may be placed within housing 142, as described above, and secured in place through compression forces exerted by pins 160. Once so positioned, treatment chamber 114 may be sealed within a sterile environment until required at the surgical site. In this manner, treatment chamber 114 may house device 157 from the point of manufacture to the operating room, at which treatment chamber 114 may be removed from its sterile enclosure for connection into a treatment system, as will be described hereinbelow. Device 157, therefore, need not be manipulated at the surgical site prior to treatment thereof through the method of the present invention, and instead may simply be applied as delivered into a treatment system immediately prior to implantation.

Treatment Procedure

A test article was inspected and cleaned with alcohol, and then placed in treatment chamber 14 as described above. A 250 ml reservoir of saline was placed in a water bath at 37° C. Once the saline reached equilibrium temperature, the open ends of conduit sections 30, 34 were placed in the reservoir. Pump 16 was activated and adjusted to a flow rate of 600 ml per minute to pump the saline through system 10 for ten minutes to rinse the system and to test for potential leakage.

In "direct connection" tests, positive polarity electrical connections are made to electrodes 60, 70, and a negative polarity electrical connection is made to electrode 80. Moreover, in "direct connection" tests, electrode 70 is positioned so as to make direct contact with at least a portion of the test biomaterial article. In the case of valve prosthesis 56, electrode 70 may be placed in direct contact with the pyrolytic carbon leaflets when conducting a "direct connection" test.

Power supply 18 was calibrated to provide a signal having positive going (2.25 V/2.25 mA DC offset, a 4.5 V peak pulse which correlates to a 4.5 mA current. The current is derived by making a differential measurement of the signal across a precision 1 kΩ resistor. A duty cycle of 41.6% was assigned (25 ms ON (+4.5 V) and 60 ms OFF (0 V)).

Pump 16 is then turned off and system 10 drained of the saline. A 250 ml reservoir of sample fluid (human whole blood, animal whole blood, blood serum, platelet rich plasma, platelet poor plasma, etc.) replaces the saline reservoir in the water bath set to 37° C. Pump 16 is again activated to expose system 10 to the sample fluid. Upon completion of the test period, the sample fluid is drained from system 10 and system 10 is then immediately flushed with saline through the process described above.

The test article is then removed from treatment chamber 14, rinsed in saline, and placed in a solution of gluteraldehyde to arrest further cell action and interaction. The test article is then dehydrated with ethanol to enable assessment of the article surface within the scanning electron microscope vacuum chamber.

Figure 10:
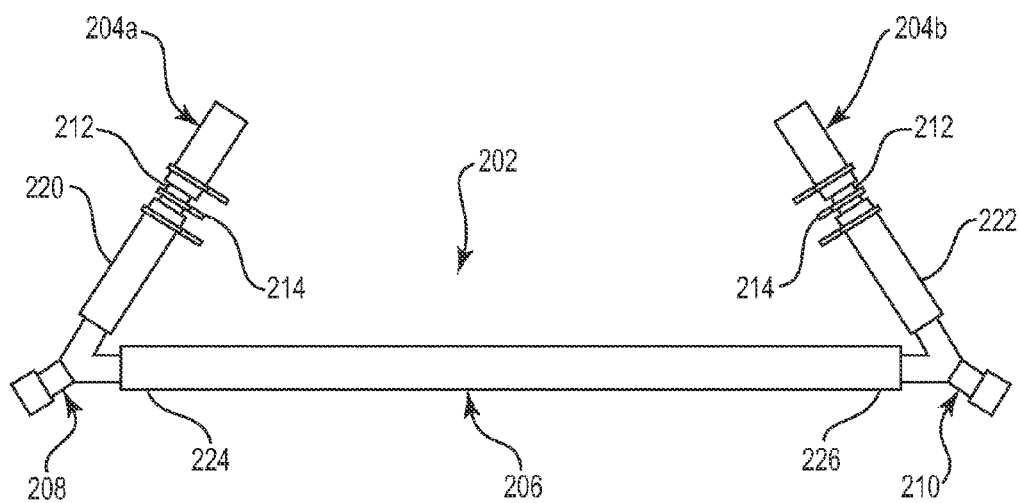
FIG. 10 is an isolation view of a portion of a treatment system of the present invention.

A further treatment procedure of the present invention involves a device 157 disposed in treatment chamber 114, as described above. Treatment chamber 114 may be placed into a bypass circuit 202 illustrated in FIG. 10. Bypass circuit 202 may be adapted to be integrated into a heart bypass system used in connection with patients undergoing procedures in which the heart is temporarily stopped. The cardiopulmonary bypass system employs tubing coupled to components such as a blood reservoir, a pump, an oxygenator, and possibly other components. It is contemplated that bypass circuit 202 may be utilized in conjunction with conventional cardiopulmonary bypass systems.

Bypass circuit 202 includes a chamber branch 204*a*, 204*b* for coupling to treatment chamber 114, and a non-chamber branch 206. The respective branches of bypass circuit 202 include biocompatible tubing for conveying treatment fluid therethrough, as well as first and second terminal coupling joints 208, 210 for coupling bypass circuit 202 to, for example, a cardiopulmonary bypass system. Chamber branch 204*a*, 204*b* may include one or more electrically conductive tube connectors 212 respectively connecting tube sections of chamber branch 204*a*, 204*b*. Tube connectors 212 may be fabricated from, for example, an electrically conductive metal such as titanium, or any other electrically conductive material having an electrical resistance of less than about 0.5 ohms. In one embodiment, tube connectors 212 may substantially comprise a tubular segment having an outer diameter which may be received in the lumens of respective tube sections of chamber branch 204*a*, 204*b*. A variety of configurations for tube connectors 212, however, is contemplated by the present invention to establish an electrical connection point exposed to the treatment fluid upstream and/or downstream of treatment chamber 114.

Figure 11:
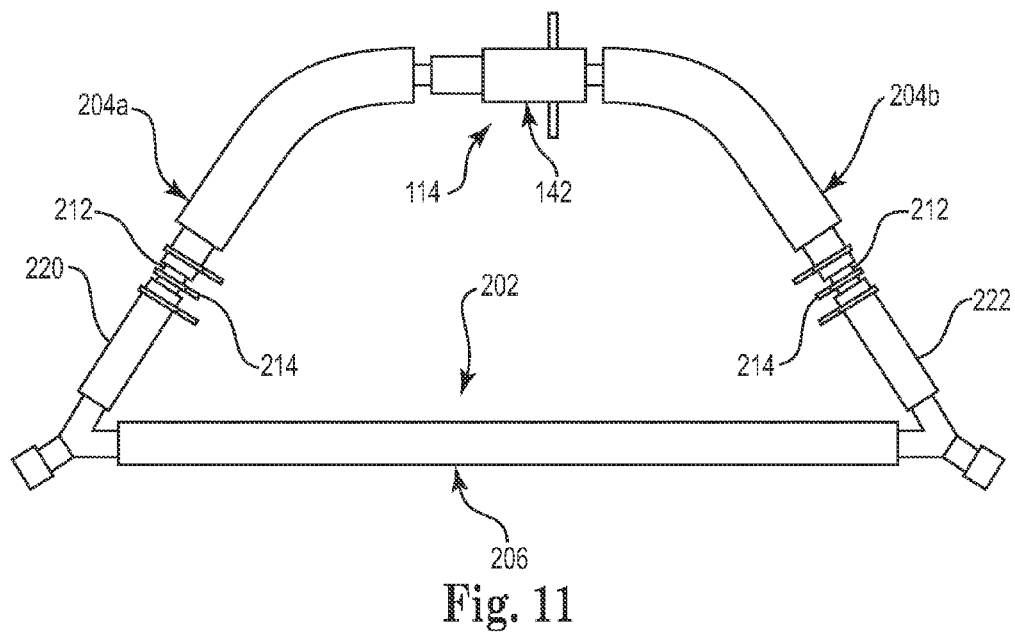
FIG. 11 is an isolation view of a portion of a treatment system of the present invention.

Treatment chamber 114 may be coupled to bypass circuit 202 as illustrated in FIG. 11. In one embodiment, treatment chamber 114 is oriented such that treatment fluid inlet 150 is coupled to a fluid inlet portion 204*a* of chamber branch 204*a*, 204*b*. In this manner, treatment fluid may be caused to be conveyed through device 157 in a manner which contacts all surfaces to be treated.

Figure 12:
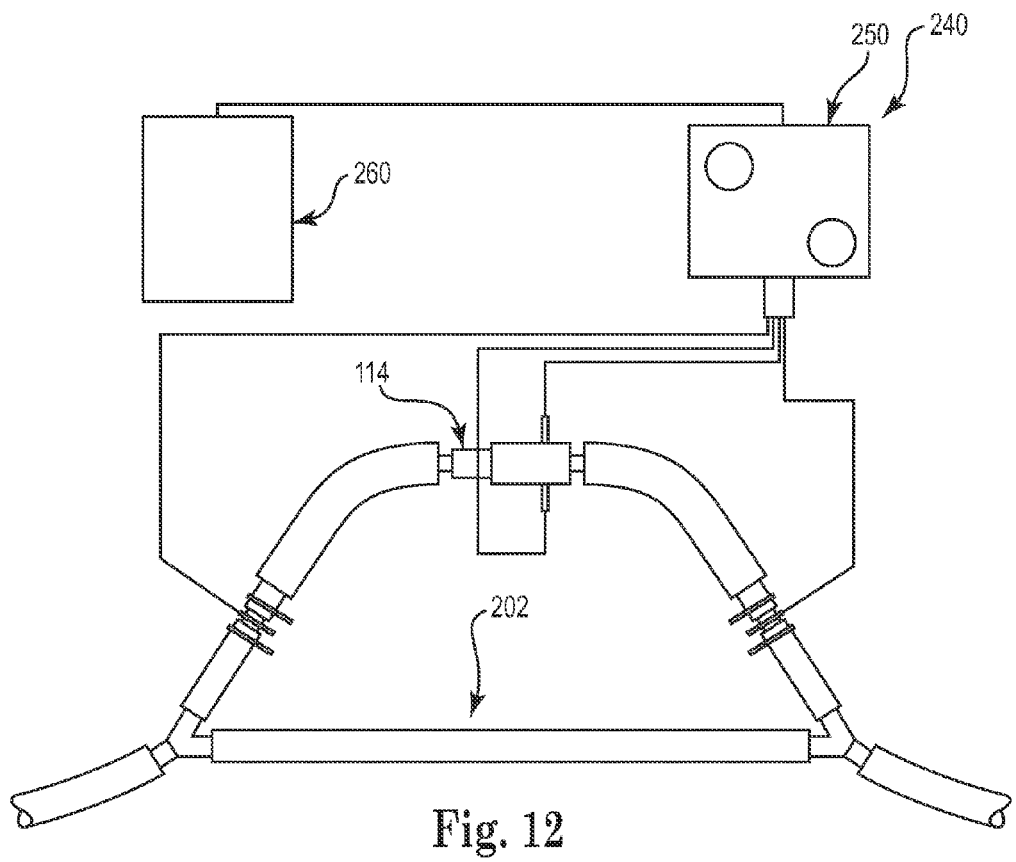
FIG. 12 is a schematic illustration of a treatment system of the present invention.
Figure 13:
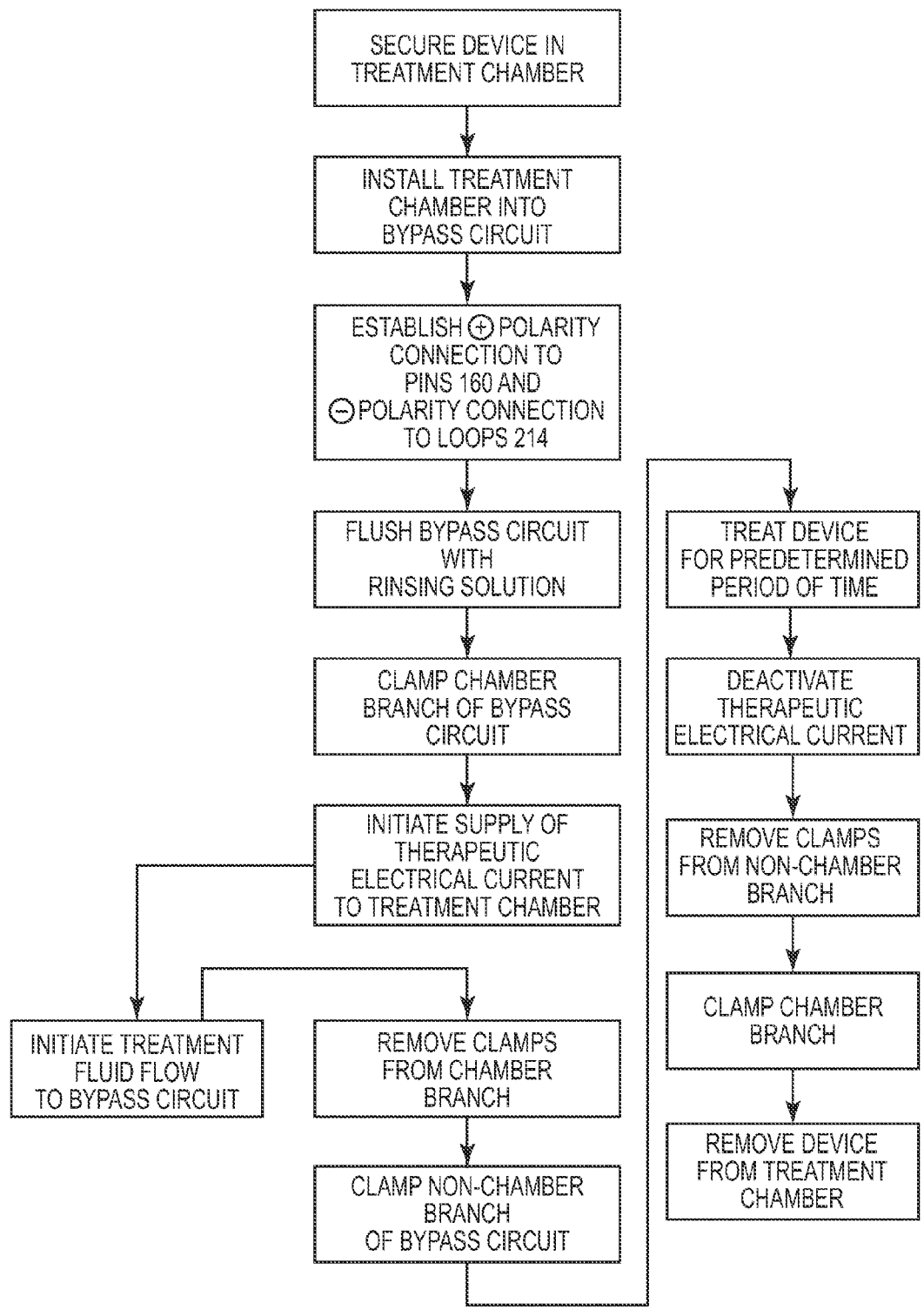
FIG. 13 is a flow diagram representing a treatment method of the present invention.
Figure 14:
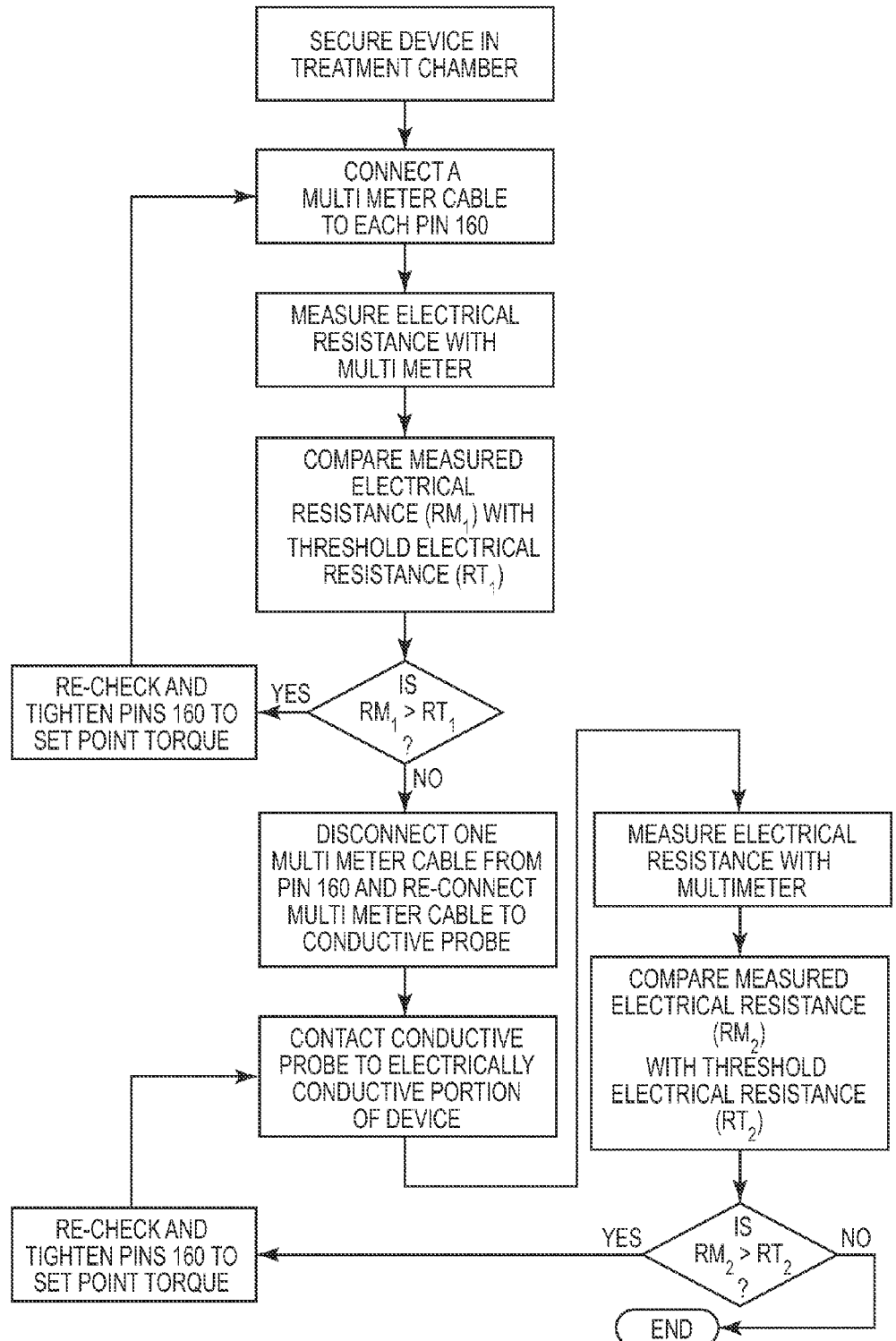
FIG. 14 is a flow diagram representing a treatment system qualification method of the present invention.

A treatment system 240 of the present system is illustrated in FIG. 12. In one embodiment, treatment system 240 includes treatment chamber 114, bypass circuit 202, an electrical energy source 250, and an oscilloscope 260.

In one embodiment, prior to connecting treatment chamber 114 to chamber branch 204*a*, 204*b*, device 157 may be checked for proper securement and positioning within housing 142. To do so, treatment chamber 114 may be held or otherwise suspended in a substantially vertical orientation with treatment fluid inlet 150 being oriented substantially vertically above treatment fluid outlet 152. A technician may then verify that device 157 is properly positioned, including valve leaflets 196 being oriented in a fully open condition. In the event that such leaflets are not fully opened, pins 160 may be loosened with a torque wrench (not shown) to reduce the compression forces upon device 157 to an extent at which the valve leaflets 196 hang under the force of gravity to an open position. The technician may then re-tighten pins 160 using the torque wrench to a desired extent, such as about 8 in oz. As described above, the torque wrench may engage pins 160 at actuation ends 160a, which are configured to engage with a tool fitting of the torque wrench.

A multimeter (not shown) may be utilized in the set up of the treatment system of the present invention to ensure sound electrical connections. The multimeter may be used outside of the sterile field, though in some embodiments, the multimeter cables may be sterilized for connection to the treatment system. In one example, the multimeter cables may be releasably coupled to each of pins 160 of treatment chamber 114 to ensure that good electrical connection is established across device 157, from a first pin 160 to a first conductor clip 198, to device 157, to a second conductor clip 198, and finally to a second pin 160. If the reading on the multimeter is unexpectedly high, such as greater than about 0.5 ohms, the torque wrench may be applied to pins 160 to establish greater electrical connection as between the parts described above.

Another electrical connection test which may be performed is to releasably secure one multimeter wire to one of pins 160, and the other multimeter wire to an electrically conductive probe, and to then insert the electrically conductive probe into treatment chamber 114 to come into contact with device 157. In one embodiment, the electrically conductive probe may be sequentially contacted to each of the prosthetic valve leaflets 196, ensuring an expectedly low resistance reading on the multimeter. For example, the resistivity reading on the multimeter upon contact between the electrically conductive probe and a leaflet in the arrangement described above may be less than about 1.5 ohms.

With reference back to FIG. 12, positive polarity wire leads from the electrical energy source 250 are connected to each of pins 160, while negative polarity wire leads from electrical energy source 250 are connected to conductor loops 214 which are in electrical connection with tube connectors 212. With oscilloscope 260 connected to electrical energy source 250, and with treatment chamber 114 securely coupled to chamber branch 204a, 204b, bypass circuit 202 may be flushed with a rinsing solution such as saline or lactated ringers solution. Prior to instituting treatment fluid flow through bypass circuit 202, clamps may be placed at first and second clamping positions 220, 222 of chamber branch 204a, 204b to initially cause treatment fluid flow only through non-chamber branch 206. Once such clamps are in place, electrical energy source 250 may be activated to begin supplying electrical energy to the various leads connected to the treatment system. The clamps may then be removed from first and second clamping positions 220, 222, while a second set of clamps may be applied to third and fourth clamping positions 224, 226 at non-chamber branch 206 to allow full treatment fluid flow through chamber branch 204a, 204b and treatment chamber 114. In some embodiments, only a single clamp need be applied at any suitable location of non-chamber branch 206 to allow full treatment of fluid flow through chamber branch 204a, 204b.

While treatment fluid flow is passing through treatment chamber 114, electrical current is supplied to pins 160, and ultimately to device 157 through the electrical connections described above. The electrical current supplied from electrical energy source 250 has been described herein, and, in one embodiment, may include a pulsatile delivery of about 3.75 mA+/−0.25 mA. However, such electrical current characteristics may be modified as needed to perform the desired treatment of various devices 157 at treatment chamber 114. In one example, such electrical current is provided to treatment chamber 114 for a period of about 30 minutes, after which the electrical energy source 250 is deactivated. The one or more clamps applied to non-chamber branch 206 may then be removed, and inlet side 204a of chamber branch 204a, 204b may be clamped at first position 220 to allow the treatment fluid to drain from treatment chamber 114. Once the treatment fluid has substantially drained from treatment chamber 114, outlet side 204b of chamber branch 204a, 204b may be clamped at a second position 222 to completely isolate treatment chamber 114 from treatment fluid flow passing through bypass circuit 202. Treatment chamber 114 is then disconnected from electrical energy source 250 and from chamber branch 204a, 204b of bypass circuit 202. In some embodiments, the multimeter cables may be reattached to each of pins 160 to ensure that electrical conductivity remains across the circuit described above. The resistivity across such circuit should be less than an expected threshold, such as less than 1.0 ohms, to ensure that treatment of device 157 was accomplished. If a higher resistance value is indicated by the multimeter, the device 157 within treatment chamber 114 would be discarded.

To remove device 157 (and holder 159) from treatment chamber 114, first and second portions 144, 146 of housing 142 may be separated, followed by loosening pins 160 with a torque wrench to an extent which results in device 157 and holder 159 being free from the compression forces previously provided by pins 160. A long tool, such as a hemostat, may then be utilized to lift device 157 and holder 159 out from interior 149 of second portion 146. To prepare device 157 for implantation, holder 159 and device 157 are rinsed with saline, and conductor clips 198 are removed. At this juncture, device 157 may be implanted in the patient using holder 159 in a conventional fashion.

EXAMPLES

The invention is further and more specifically illustrated by the following examples and tests.

Example 1

A control experiment was conducted using whole human blood donated within three hours of testing. The whole human blood was pumped through system 10 in the absence of applied electrical energy, and was contacted with a pyrolytic carbon heart valve prostheses at test chamber 14. This test was continued for 30 minutes.

Figure 4:
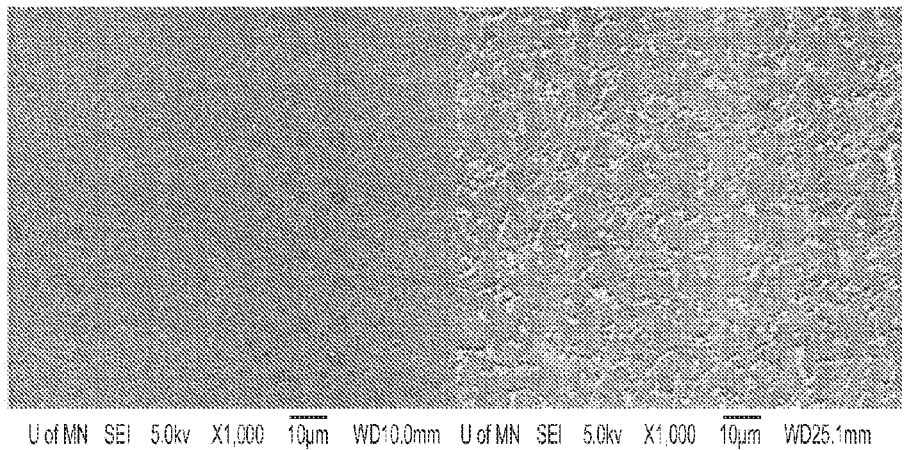
FIG. 4 is a SEM image comparison between a first control test article exposed to whole human blood and a second control test article not exposed to blood.

FIG. 4 illustrates two scanning electron microscope (SEM) slides taken at 1000× magnification. A photograph of a clean, untested pyrolytic carbon valve prosthesis leaflet is shown on the left, and a pyrolytic carbon valve prosthesis leaflet taken from the test article following the control test is shown on the right. It is clear from this control sample that blood platelets are adhered and spread across the surface of the pyrolytic carbon under typical blood exposure conditions, such as those found in vivo. The conditions of the control experiment substantially replicate conditions experienced in vivo for implantable medical articles.

Example 2

Figure 5:
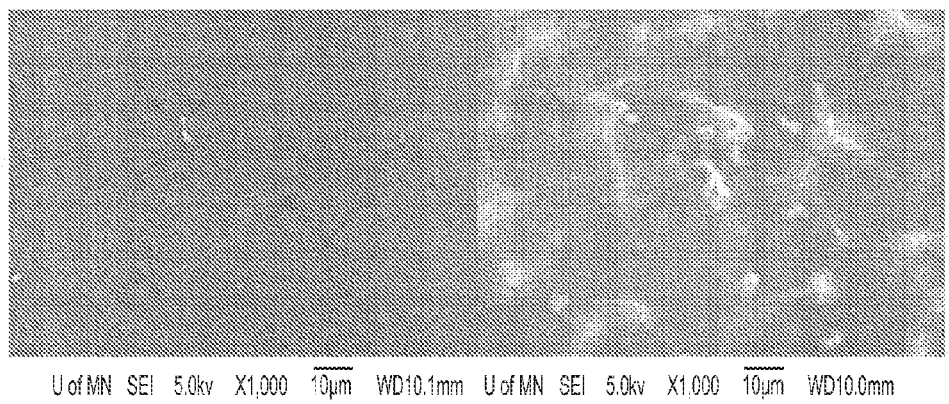
FIG. 5 is a SEM image comparison between a third control test article exposed to whole human blood in an unstimulated environment, with a fourth test article exposed to whole human blood in a stimulated environment.

A sample of whole human blood was separated into two aliquots, with a first aliquot being tested through the "direct connection" procedure described above for 45 minutes. The second aliquot of whole human blood was cycled through system 10 and contacted with a pyrolytic carbon test article in the absence of electrical energy application as a control for 45 minutes. The SEM slides of FIG. 5 demonstrate an image of the control test article surface on the right, and an image of the test article surface used in the "direction connection" test on the left.

It is clear from visual comparison of the SEM slide that the test article surface exposed to the electrical energy is substantially clear of adhered platelets, while the control test article exhibits significant platelet confluency at its surface. A graphical pixilation analysis was performed to derive a quantitation of blood platelet cell presence at the respective test article surfaces. The graphical pixilation analysis was performed by colored pixel count of the SEM images, wherein individual pixel colors other than black were considered adhered platelet cells. The graphical pixilation count analysis of test article surface exposed to electrical energy revealed about 2.5% platelet adhesion, while the control test article surface exhibited about 59.1% platelet cell confluency.

Example 3

A sample of human platelet rich plasma (PRP) was separated into three aliquots with a first aliquot being tested through the "direct connection" procedure described above in a "stagnant" flow regime, wherein the test articles are exposed to a stagnant volume of test fluid for the test period. A first pyrolytic carbon test article was exposed to the first aliquot of PRP in the presence of the electrical energy application described above for 15 minutes. The first pyrolytic carbon test article was then exposed to whole human blood from the PRP donor in a pulsed flow regime for 45 minutes in the absence of applied electrical energy.

A second pyrolytic carbon test article was tested similarly to the first pyrolytic carbon test article, except that the second test article was exposed to PRP in the presence of applied electrical energy for 30 minutes prior to exposure to whole human blood from the PRP donor for 45 minutes in the absence of applied electrical energy.

Control pyrolytic carbon test articles were exposed to PRP in the stagnant chamber for 15 and 30 minutes, respectively, without applied electrical energy, and then exposed to whole human blood from the PRP donor in a pulsed flow regime for 45 minutes in the absence of applied electrical energy.

The test article surfaces were assessed with SEM, and the first and second test articles exhibited significantly less adhered platelets than the amount of adhered platelets observed on the control test article.

Example 4

A sample of human platelet poor plasma (PPP) was separated into three aliquots for testing in connection with three test articles. A first pyrolytic carbon test article was exposed to the first aliquot of PPP in the presence of direct connection electrical energy for 15 minutes. The first pyrolytic carbon test article was then exposed to whole human blood from the PPP donor in a pulsed flow regime for 45 minutes in the absence of applied electrical energy.

A second pyrolytic carbon test article was exposed to PPP in the presence of applied electrical energy for 30 minutes prior to exposure to whole human blood from the PPP donor for 45 minutes in the absence of applied electrical energy.

Control pyrolytic carbon test articles were exposed to PPP in the stagnant chamber for 15 and 30 minutes, respectively, without applied electrical energy, and then exposed to whole human blood from the PPP donor in a pulsed flow regime for 45 minutes in the absence of applied electrical energy.

The test article surfaces were assessed with SEM, and the first and second test articles exhibited significantly less adhered platelets than the amount of adhered platelets observed on the control test article.

Example 5

Bovine blood platelets labeled with indium-111 were used as the sample fluid in a test to determine the ability of passivated test article surfaces to remain effective in the prevention of platelet adhesion over time without continued electrical stimulation. In this "pre-treatment" exercise, four pyrolytic carbon test articles were exposed to the bovine blood for 60 minutes. One of such test articles was electrically stimulated for the entire 60 minute test period. Two test articles were stimulated for 30 minutes during the bovine blood exposure, and then disconnected from the electrical energy for the remaining 30 minutes of the test period. One test article was unstimulated throughout the entire 60 minute test period. The electrical stimulation was conducted at the parameters described above.

Figure 7:
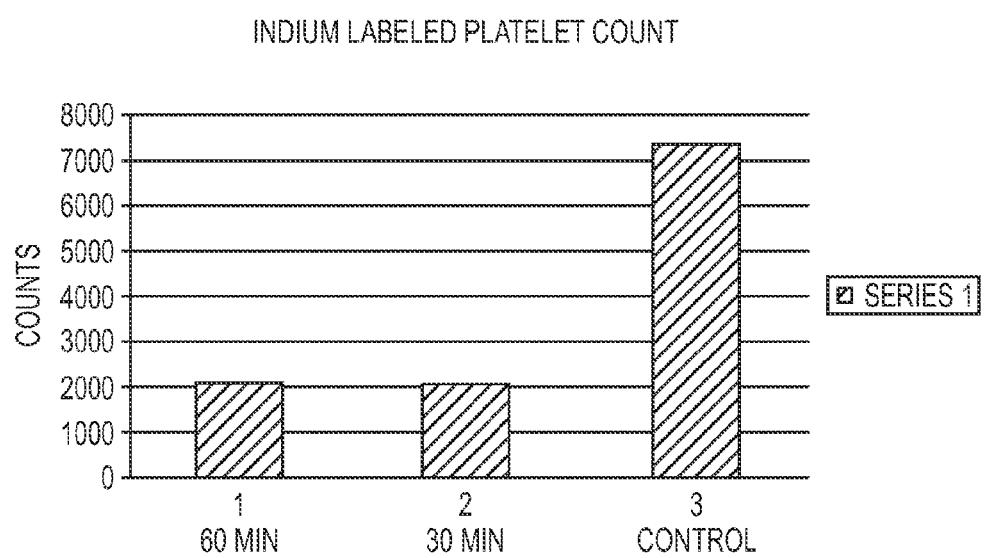
FIG. 7 is a radioactive count chart illustrating platelet concentrations at test articles exposed to different test environments.

The chart of FIG. 7 illustrates radioactive counts for each of the three test groups described above, wherein the radioactive counts are indicative of platelet concentration at the respective test article surface. As demonstrated therein, it appears that pre-treatment of the test article with stimulation in the presence of blood is also effective in inhibiting platelet adhesion even in the absence of continued electrical stimulation. Specifically, the "Group 2" test article surfaces, which were electrically stimulated only for the first 30 minutes of the 60 minute test period, exhibited post-test platelet concentrations similar to the post-test platelet concentrations at the test article surfaces of "Group 1", which received electrical stimulation throughout the 60 minute test period. By contrast, the "Group 3" test article surfaces, which were exposed to blood in the absence of electrical stimulation, exhibited post-test platelet concentrations several fold higher than the platelet concentrations exhibited by either of the stimulated group test articles.

Analysis

A gel electrophoresis analysis was performed on the test article surfaces regarding the blood proteins present thereat. Gel electrophoresis was performed through the use of the microplates procedure of a BCA™ protein assay kit available from Pierce, a division of Thermo Fisher Scientific, Inc., of Rockford, Ill. Proteins taken from 6 test articles, 3 of which were tested in a "stimulated" environment, and the remaining 3 were tested in an "unstimulated" environment by being exposed to blood in the absence of applied electrical energy.

FIG. 6 illustrates results for "stimulated" samples (those tested with exposure to therapeutic electrical energy) versus unstimulated samples (control). The dark bands between 65 and 75 kD indicate the presence of albumin. It appears that the presence of albumin is enhanced by 5-10× in the stimulated group, based on the results of the protein assay. It is well understood that albumin stabilizes charges on materials thereby preventing electric charge-related platelet interactions. The presence of albumin at the surface therefore plays a role in inhibiting platelet interaction/adhesion with the test article surface. It is a surprising result of the above-described tests, however, that application of the utilized levels of electrical energy modulates the preferential adsorption of at least albumin to the test article surface, in that albumin adsorption appears to be significantly preferentially promoted. Such preferential promotion of albumin adsorption is demonstrated by the enhanced albumin presence in the gel electrophoresis slides illustrated in FIG. 6, as well as in the protein assay analyses. It is theorized that the preferential promotion of at least albumin adsorption on the stimulated article surface is caused by the electrical charge provided at the surface through the applied electrical energy.

FIG. 6 further illustrates a conformational alteration of fibrinogen in the stimulated group, as compared to the fibrinogen found on the unstimulated test article surfaces. As described above, the three bands around 50 kD represent alpha, beta, and gamma fibrinogen. The unstimulated article surfaces exhibit all three fibrinogen conformations with approximately similar intensity response through gel electrophoresis. The stimulated test article surfaces, however, exhibited a significantly higher concentration of beta fibrinogen, and a lower concentration of at least alpha fibrinogen and possibly a lower concentration of gamma fibrinogen as well. Of the three fibrinogen conformations, alpha fibrinogen is the lowest molecular weight, and gamma fibrinogen is the highest molecular weight. The concentration changes illustrated by the gel electrophoresis intensity changes in FIG. 6 likely reflects a conformational alteration of the fibrinogen that is related to or induced by electrical stimulation.

The protein assay described above further confirms a substantial increase in fibrinogen concentration at the stimulated test article surfaces, as compared to the fibrinogen concentrations found on the unstimulated test article surfaces. The fibrinogen detected at the surfaces at the stimulated group, however, was conformationally altered as described above. It was determined that the fibrinogen concentration of the stimulated group was 5-10× greater than the fibrinogen concentration of the unstimulated group, thus evidencing a preferential promotion of at least conformationally altered fibrinogen adsorption on the stimulated article surface.

It is theorized that the alteration of fibrinogen receptors caused by the exposure to the therapeutic electrical energy inhibits the binding of further fibrinogen to the surface. The alpha chain of fibrinogen contains the RGDS sequence necessary for platelet interactions. The gamma chain of fibrinogen holds the dodecapeptide sequence (including the RGDS) that can be used for platelet aggregation. Reducing or eliminating the presence of alpha and/or gamma fibrinogen, as seen in the gel electrophoresis images of the stimulated group, may therefore correspondingly inhibit platelet adhesion and aggregation. One explanation for this effect may be that the reduced reactivity of the stimulated surfaces could be explained through an interference of the electrical current with the Vroman effect resulting in: 1) alterations of the molecule of fibrinogen deposited; 2) modifications on the characteristic conformational changes that occur after the adsorption of fibrinogen to the surface; and 3) albumin related cross-linking mechanisms altering the properties of the adsorbed fibrinogen.

Commentary

In view of the above examples and analysis, Applicant has determined that, in one embodiment, therapeutic electrical energy applied to a biomaterial surface, while such surface is exposed to a blood protein-containing fluid such as whole blood or plasma, can passify such biomaterial surface, at least against thrombosis. These studies have further shown that biomaterial surface passivation may be accomplished in a "pre-treatment" arrangement, wherein the biomaterial surface undergoes a passivating procedure and is subsequently placed into a blood platelet-contacting environment. The passivated biomaterial surface exhibits ongoing thromboresistant properties even in the absence of continuing surface passivation. In effect, therefore, a biomaterial surface may be passivated in advance of implantation, with the passivated biomaterial surface remaining effective, at least in the case of thromboresistance, for a significant length of time subsequent to implantation. Accordingly, the methods and materials of the present invention may be utilized, for example, to prevent thrombosis formation in devices such as vascular stents by pre-treating blood-contacting surfaces thereof in the presence of a relatively small amount of the respective patient's blood or plasma prior to device implantation into the patient.

The electrical stimulation described above with reference to the examples, is merely representative of various electrical energy magnitudes that may be useful in passivating biomaterial surfaces. For example, the applied electrical current in the above examples of electropositive 4.5 mA directed to a pyrolytic carbon material having a surface area of about 12.4 $cm^2$ provides a current density of about 0.35 $mA/cm^2$. As described in our co-pending patent application Ser. No. 11/402,463 entitled "System for Conditioning Surfaces in Vivo", the content of which being incorporated herein by reference, an electropositive current density of between about 0.001 and about 1.0 $mA/cm^2$ may also be useful in the present application. Applicant believes that a current density of at least about 0.1 $mA/cm^2$ may be most beneficial for the purposes described herein, depending upon the electrical conductivities of the biomaterials at issue. An upper threshold on the electropositive current density provided at the biomaterial surface for therapeutic conditioning thereof in the present application may be limited only by the current density threshold above which undesired and/or permanent damage to such biomaterial or interfacing material may occur.

For the purposes of this application, therefore, the term "therapeutic electrical energy" shall mean electrical energy that is effective in generating an electropositive current density at the subject biomaterial surface at a magnitude sufficient to passivate the biomaterial surface through exposure of the biomaterial surface to the electrical energy in the presence of blood or plasma. In one embodiment, such therapeutic electrical energy results in an electropositive current density at the biomaterial surface being treated of at least about 0.1 $mA/cm^2$.

As also described above, a further aspect of the present invention is the surprising finding that the deposition of certain blood proteins and/or blood protein concentrations at a biomaterial surface is effective in passivating such biomaterial surface. One passivating material of the present invention is a conformationally altered fibrinogen, and specifically a fibrinogen with a relatively high concentration of beta fibrinogen and/or relatively low concentrations of alpha fibrinogen and/or gamma fibrinogen. Applicant has determined that the presence of such modified fibrinogen at the biomaterial surface at a concentration of at least about 5-10× the concentration of unmodified fibrinogen at an unstimulated surface exposed to blood or plasma for at least about 15 minutes may be effective in passivating the biomaterial surface. As such, Applicant envisions a variety of techniques for depositing a passivating agent, such as conformationally modified fibrinogen, at the biomaterial surface for passivating such biomaterial surface. For example, such a passivating agent may be isolated and used as needed, such as by depositing the passivating agent at a biomaterial surface prior to biomaterial implantation into a patient. Such treatment of the blood-contacting surface of the biomaterial may be performed immediately prior to implantation or significantly prior to implantation, with the passivating agent retaining its passivating properties for a significant period of time subsequent to implantation.

An overall impact, therefore, of the present invention is the prevention of platelet adhesion and thrombogenesis on biomaterial surfaces, including artificial implants, transplants, and native tissue, through the provision of certain modified and/or unmodified blood proteins at such surfaces. In one embodiment, such blood proteins may be provided at the biomaterial surfaces through the application of therapeutic electrical energy to the surface while the surface is in the presence of blood or plasma. Other techniques, however, for the provision of effective passivating agents on target surfaces are envisioned in the present invention.

The invention has been described herein in considerable detail in order to comply with the patent statutes, and to provide those skilled in the art with the information needed to apply the novel principles and to construct and use embodiments of the invention as required. However, it is to be understood that various modifications to the invention can be accomplished without departing from the scope of the invention itself.

What is claimed is:

1. A system for passivating a biomaterial surface, said system comprising:
    (a) a treatment chamber housing defining a chamber therewithin, and having a treatment fluid inlet and a treatment fluid outlet in fluid communication with said chamber;
    (b) a treatment fluid source comprising blood or blood plasma;
    (c) a first treatment fluid conduit for conveying treatment fluid from said source to said treatment chamber;
    (d) a first electrode electrically coupled to said biomaterial surface in said chamber, said first electrode providing an electrical conduction path from said housing to said chamber; and
    (e) an electrical energy source for generating therapeutic electrical current, said electrical energy source being capable of delivering said therapeutic electrical current to said first electrode.

2. The system of claim 1, including a second electrode exposed to the treatment fluid as a return electrode electrically coupled to said electrical energy source.

3. The system of claim 1 wherein said first electrode adjustably exerts a physical force for securing said biomaterial surface within a treatment fluid flow path in said chamber.

4. The system of claim 3 wherein said first electrode is threadably engaged through said treatment chamber housing.

5. The system of claim 3, including a conductor clip electrically connecting said first electrode to said biomaterial surface.

6. The system of claim 3, including a pair of first electrodes arranged to adjustably exert substantially opposed compression forces to said biomaterial surface.

7. The system of claim 1 wherein said biomaterial surface is at least a portion of said medical article.

8. The system of claim 1 wherein said treatment chamber housing includes first and second portions fluidly sealingly engagable with one another to define said chamber, said first and second portions being disengagable to permit removal of said biomaterial surface from said chamber.

9. A system for passivating a biomaterial surface, said system comprising:
    (a) a treatment chamber housing defining a chamber therewithin, and having treatment fluid inlet and a treatment fluid outlet in fluid communication with said chamber;
    (b) a treatment fluid source;
    (c) a first treatment fluid conduit for conveying treatment fluid from said source to said treatment chamber;
    (d) a first electrode electrically coupled to said biomaterial surface in said chamber, said first electrode providing an electrical conduction path from said housing to said chamber;
    (e) a second treatment fluid conduit for conveying treatment fluid from said treatment chamber to a cardiopulmonary bypass system; and
    (f) an electrical energy source for generating therapeutic electrical current, said electrical enemy source being capable of delivering said therapeutic electrical current to said first electrode.

10. The system of claim 9, including a second electrode exposed to the treatment fluid as a return electrode electrically coupled to said electrical energy source.

11. The system of claim 9 wherein said first electrode adjustably exerts a physical force for securing said biomaterial surface within a treatment fluid flow path in said chamber.

12. The system of claim 11 wherein said first electrode is threadably engaged through said treatment chamber housing.

13. The system of claim 11, including a conductor clip electrically connecting said first electrode to said biomaterial surface.

14. The system of claim 11, including a pair of first electrodes arranged to adjustably exert substantially opposed compression forces to said biomaterial surface.

15. The system of claim 9 wherein said biomaterial surface is at least a portion of said medical article.

16. The system of claim 9 wherein the treatment fluid is blood or blood plasma.

17. The system of claim 9 wherein said treatment chamber housing includes first and second portions fluidly sealingly engagable with one another to define said chamber, said first and second portions being disengagable to permit removal of said biomaterial surface from said chamber.

* * * * *